US 9,157,054 B2

(12) United States Patent
Bhandari

(10) Patent No.: US 9,157,054 B2
(45) Date of Patent: Oct. 13, 2015

(54) DEVICE AND METHOD FOR PREPARING MICROPARTICLES

(75) Inventor: Bhesh Bhandari, Seventeen Mile Rocks (AU)

(73) Assignee: The University of Queensland, Queensland (AU)

(*) Notice: Subject to any disclaimer, the term of this patent is extended or adjusted under 35 U.S.C. 154(b) by 290 days.

(21) Appl. No.: 12/742,865

(22) PCT Filed: Nov. 14, 2008

(86) PCT No.: PCT/AU2008/001695
§ 371 (c)(1),
(2), (4) Date: Sep. 9, 2010

(87) PCT Pub. No.: WO2009/062254
PCT Pub. Date: May 22, 2009

(65) Prior Publication Data
US 2011/0008293 A1 Jan. 13, 2011

(30) Foreign Application Priority Data

Nov. 14, 2007 (AU) ................. 2007906243

(51) Int. Cl.
| A61K 9/14 | (2006.01) |
| B05D 1/12 | (2006.01) |
| C11D 17/06 | (2006.01) |
| A01N 25/28 | (2006.01) |
| A23K 1/00 | (2006.01) |
| A23K 1/16 | (2006.01) |
| A23L 1/22 | (2006.01) |
| A23L 1/30 | (2006.01) |
| A61K 8/11 | (2006.01) |
| A61K 8/73 | (2006.01) |
| A61K 9/16 | (2006.01) |
| A61K 9/50 | (2006.01) |
| A61Q 19/00 | (2006.01) |
| B01J 13/14 | (2006.01) |
| A23P 1/04 | (2006.01) |
| B01J 13/22 | (2006.01) |
| C11D 3/50 | (2006.01) |
| A61K 38/00 | (2006.01) |
| A61K 35/00 | (2006.01) |

(52) U.S. Cl.
CPC ............ *C11D 17/06* (2013.01); *A01N 25/28* (2013.01); *A23K 1/004* (2013.01); *A23K 1/164* (2013.01); *A23L 1/22016* (2013.01); *A23L 1/3006* (2013.01); *A23P 1/04* (2013.01); *A61K 8/11* (2013.01); *A61K 8/733* (2013.01); *A61K 9/1676* (2013.01); *A61K 9/501* (2013.01); *A61K 9/5073* (2013.01); *A61K 9/5089* (2013.01); *A61Q 19/00* (2013.01); *B01J 13/14* (2013.01); *B01J 13/22* (2013.01); *C11D 3/505* (2013.01); *A61K 9/5036* (2013.01); *A61K 35/00* (2013.01); *A61K 38/00* (2013.01); *A61K 2800/412* (2013.01)

(58) Field of Classification Search
CPC . A61K 2800/412; A61K 35/00; A61K 38/00; A61K 8/11; A61K 8/733; A61K 9/1676; A61K 9/501; A61K 9/5036; A61K 9/5073; A61K 9/5089
USPC ........... 424/450, 489, 490; 422/129; 427/2.14
See application file for complete search history.

(56) References Cited

U.S. PATENT DOCUMENTS

| 3,615,673 A | 10/1971 | Black et al. |
| 5,776,490 A | 7/1998 | Chu et al. ........................ 424/451 |
| 2001/0051118 A1* | 12/2001 | Mosso et al. ................... 422/186 |
| 2009/0186009 A1 | 7/2009 | Sato et al. |

FOREIGN PATENT DOCUMENTS

| EP | 0 437 360 A1 | 7/1991 |
| EP | 0437360 A1 * | 7/1991 |
| JP | 2004-300426 A | 10/2004 |
| RU | 2 170 617 C2 | 7/2001 |
| SU | 387441 | 6/1973 |
| WO | 9961145 A1 | 12/1999 |
| WO | 02/09787 A1 | 2/2002 |
| WO | 2006/021945 A1 | 3/2006 |
| WO | 2007/125915 A1 | 11/2007 |
| WO | 2008/103785 A1 | 8/2008 |

OTHER PUBLICATIONS

Corrigan, et al., "Preparation and release of salbutamol from chitosan and chitosan co-spray dried compacts and multiparticulates"; European Journal of Pharmaceutic and Biopharmaceutics 62, Apr. 2006; vol. 62, No. 3, pp. 295-305.
Intrrnational Search Report dated Feb. 13, 2009 from PCT/AU2008/001695.
European Extended Search Report dated Dec. 10, 2013 from corresponding European Patent Application No. 08850559.9; consisting of 9 pages.
Zhang, et al.; "Growth of Coatings on Nanoparticles by Photoinduced Chemical Vapor Deposition"; J. Nanopart Res, 2008; 10: 173-178.
Australian Search Report dated May 16, 2013 from corresponding Australian Application No. 2009205724, 3 pages.

* cited by examiner

*Primary Examiner* — Janet Epps-Smith
(74) *Attorney, Agent, or Firm* — Ohlandt, Greeley, Ruggiero & Perle, L.L.P.

(57) ABSTRACT

The invention provides a method for preparing microparticles comprising mixing a first cross-linkable reagent in aerosol form with a second cross-linking reagent in aerosol form to thereby to form microparticles.

16 Claims, 17 Drawing Sheets

FIG. 3

Atomiser 1

Aerosol reactant 2

Reactor/chamber

Atomiser 2 (reactant

Product flow

FIG. 6

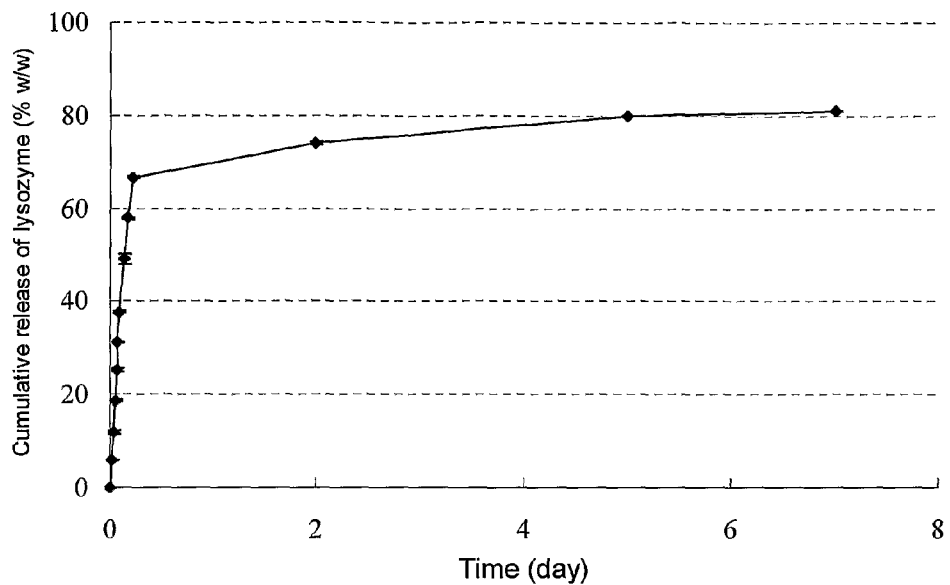
FIG. 12 Cumulative release of lysozyme from alginate gel microparticles in PBS at 37°C
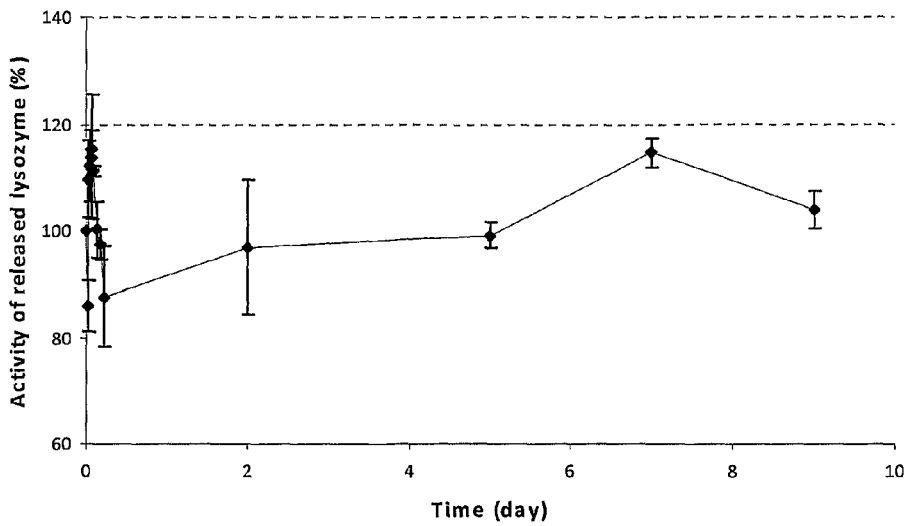
FIG. 13 Activity of lysozyme released from alginate gel microparticles in PBS at 37°C.

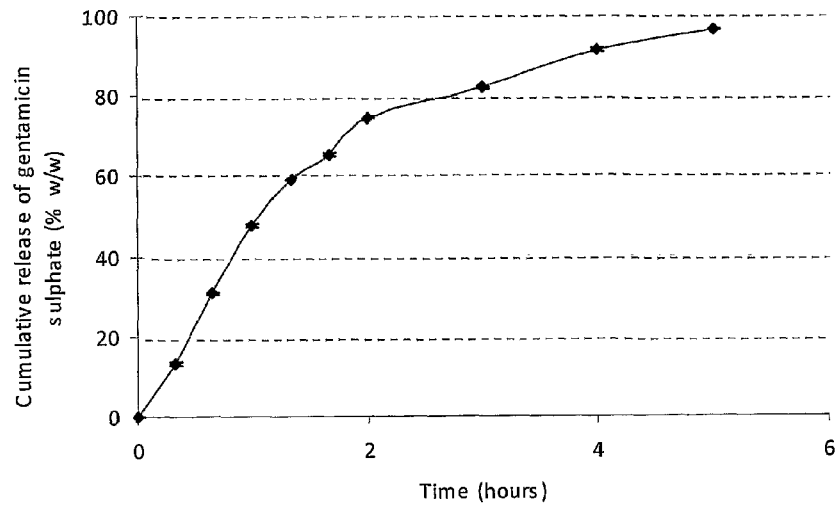
FIG. 14 Cumulative release of gentamicin sulphate from alginate gel microparticles in PBS at 37°C over 5 hours
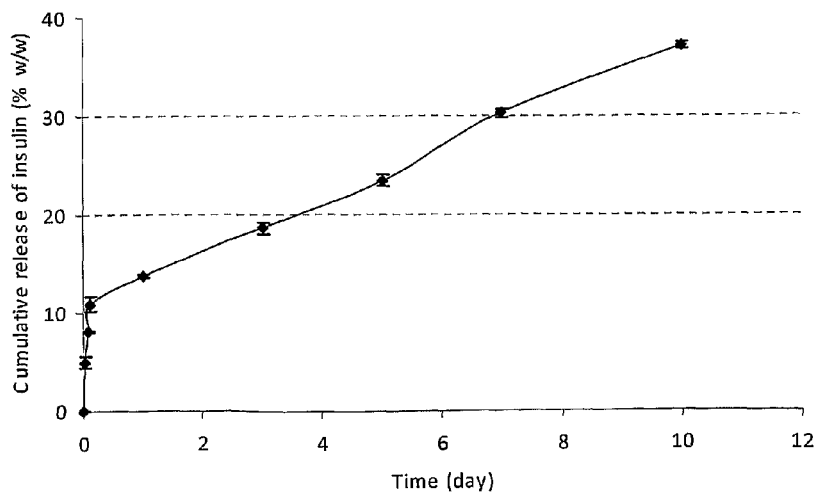
FIG. 15 Cumulative release of insulin from alginate gel microparticles in PBS at 37°C.

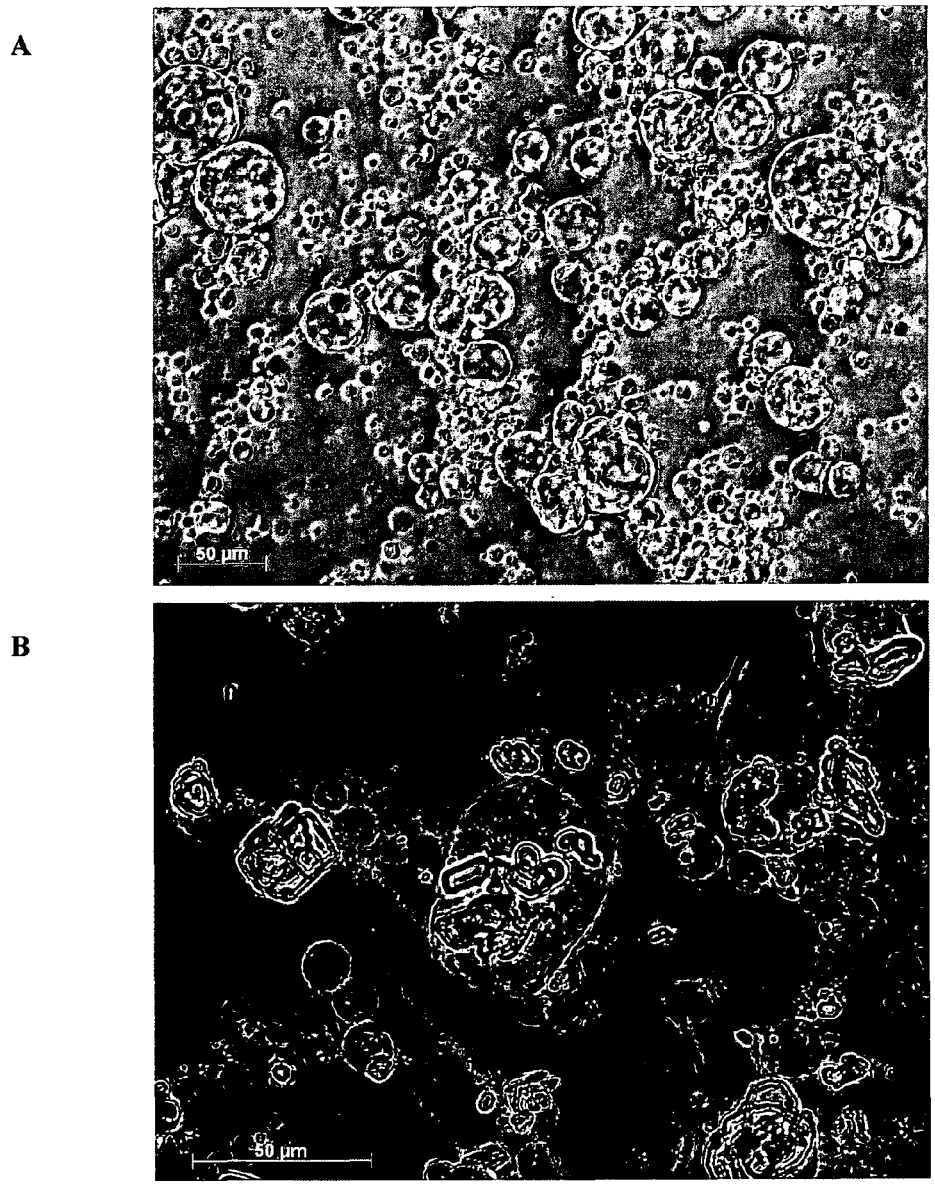
FIG. 16 Optical micrographs of (A) hydrated alginate gel particles and (B) hydrated ibuprofen-loaded alginate gel microparticles

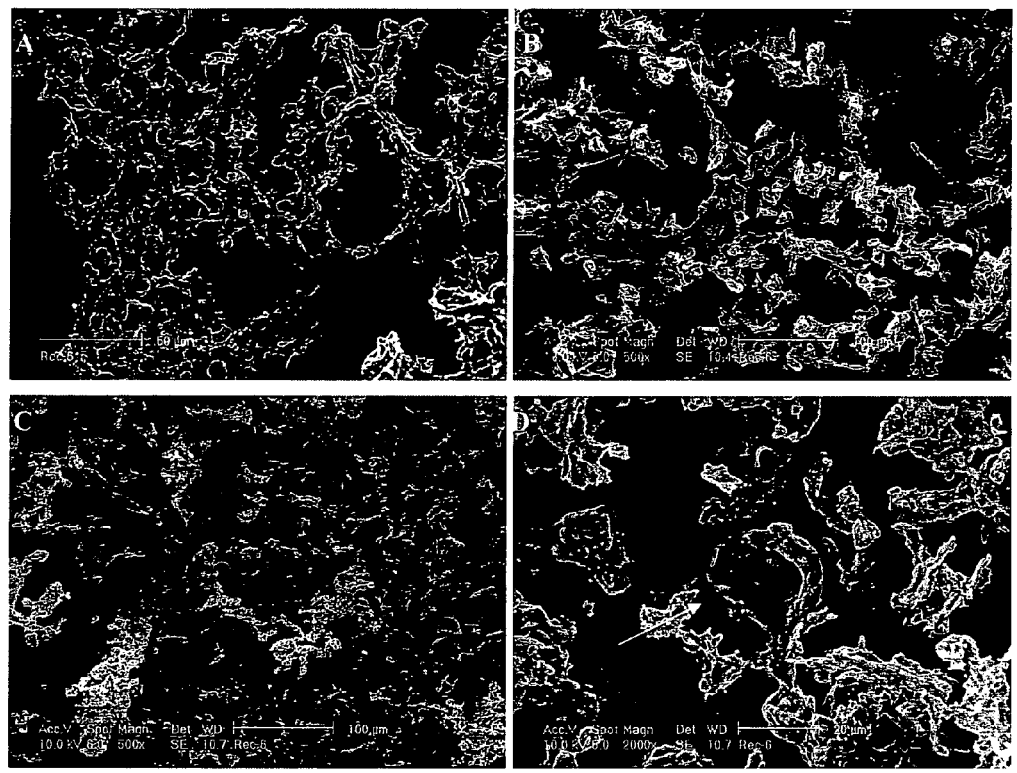
FIG. 17 Morphology of alginate gel beads after freeze drying (A) Alginate microparticles (B) Ibuprofen-loaded alginate microparticles (C, D) lysozyme-loaded alginate microparticles

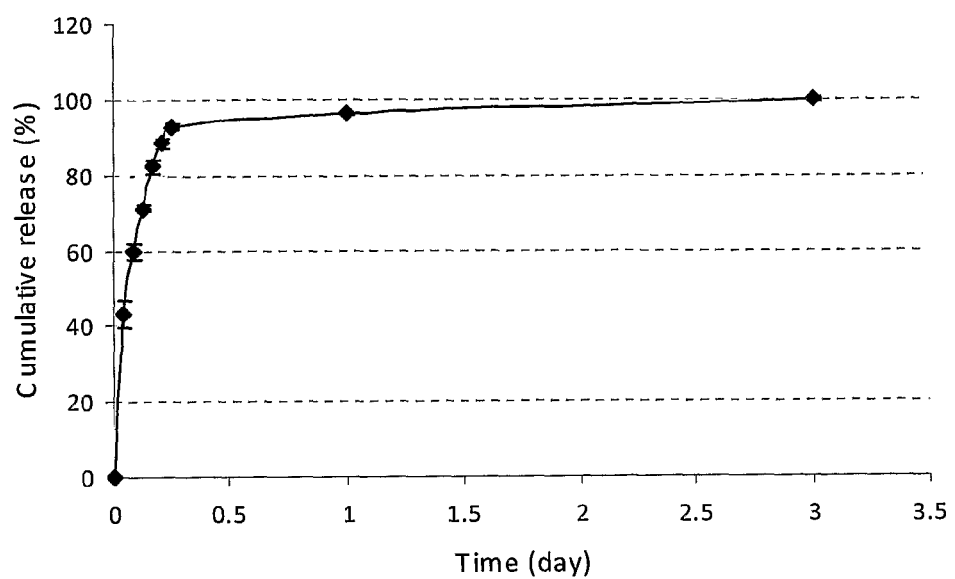
FIG. 18 Release of ibuprofen from diffusion-loaded alginate gel microparticles in PBS at 37°C.

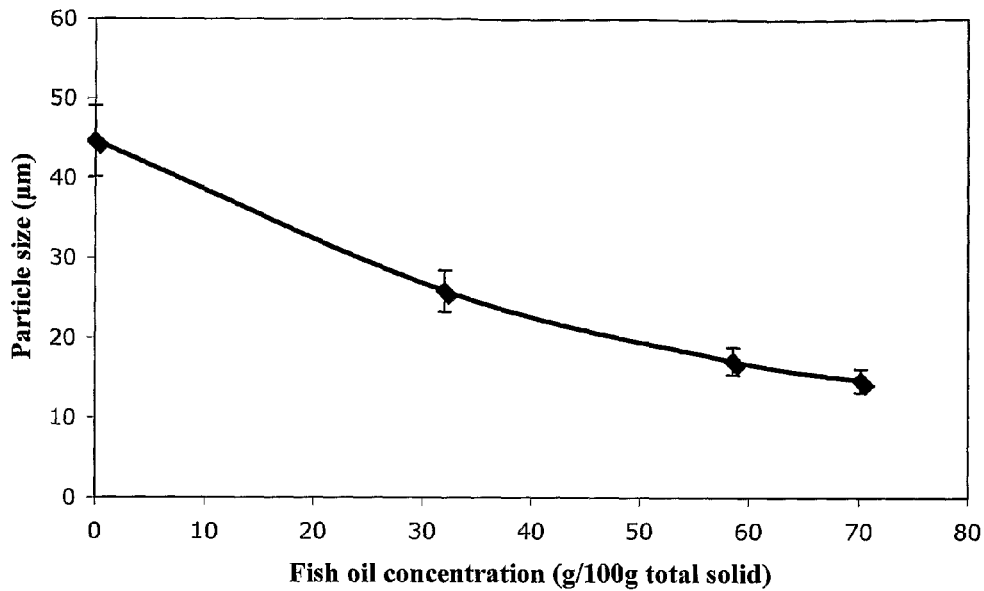
FIG. 19 Effect of increasing fish oil content (4.5g sodium alginate; 4g Hi-Cap) on mean d(0.5) microcapsule particle size.
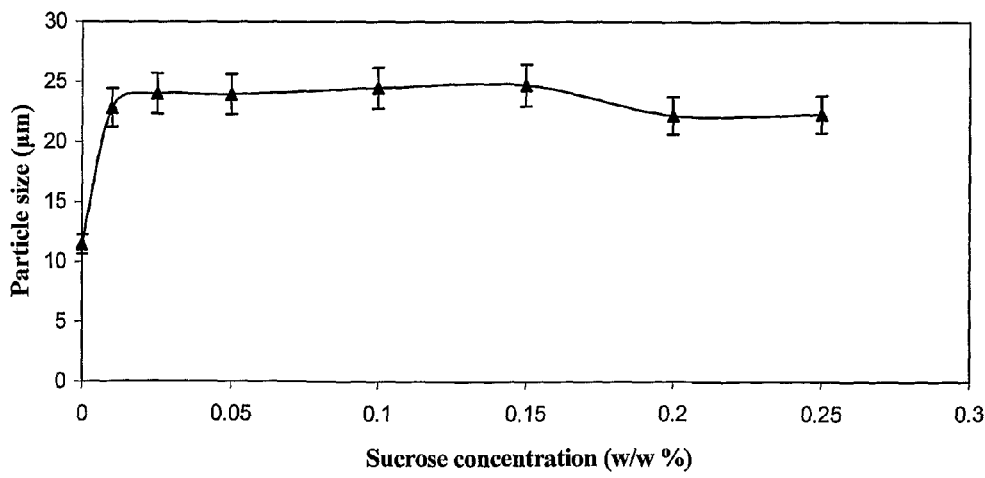
FIG. 20 Effect of solute content (sucrose concentration) on mean particle size of oil-loaded alginate microcapsule

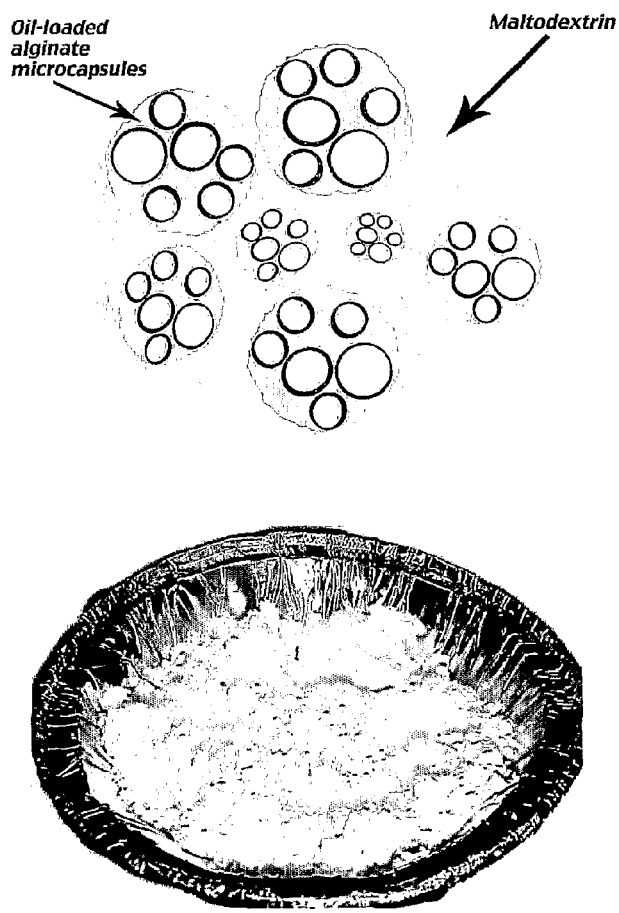
FIG. 21 Illustration of double encapsulated oil-loaded alginate microcapsules. Spray dried oil-loaded alginate microcapsules in maltodextrin at 1:3 ratio.

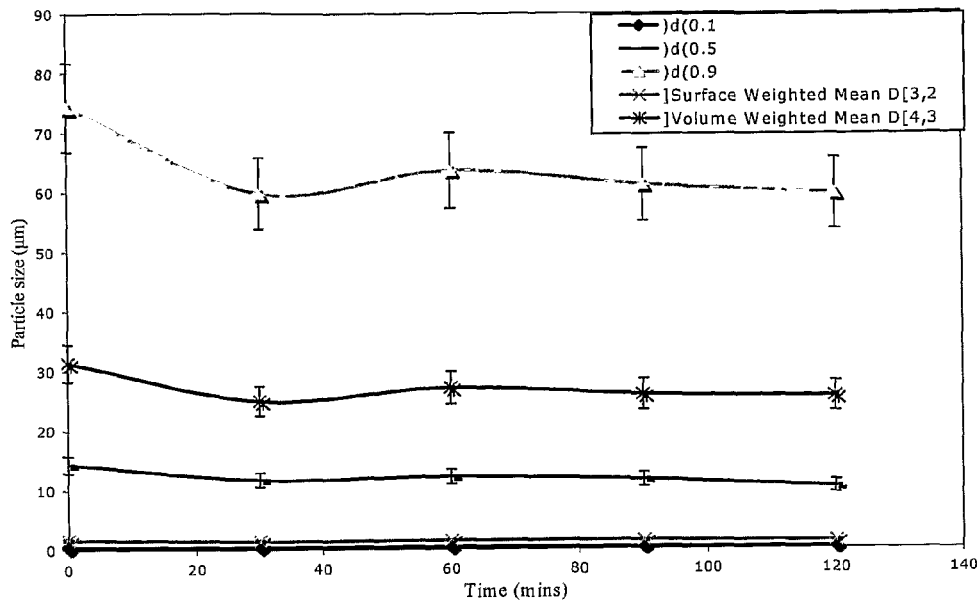
FIG. 22 Change in particle size of spray dried oil-loaded alginate microcapsules rehydrated in water over a period of 2 hours.
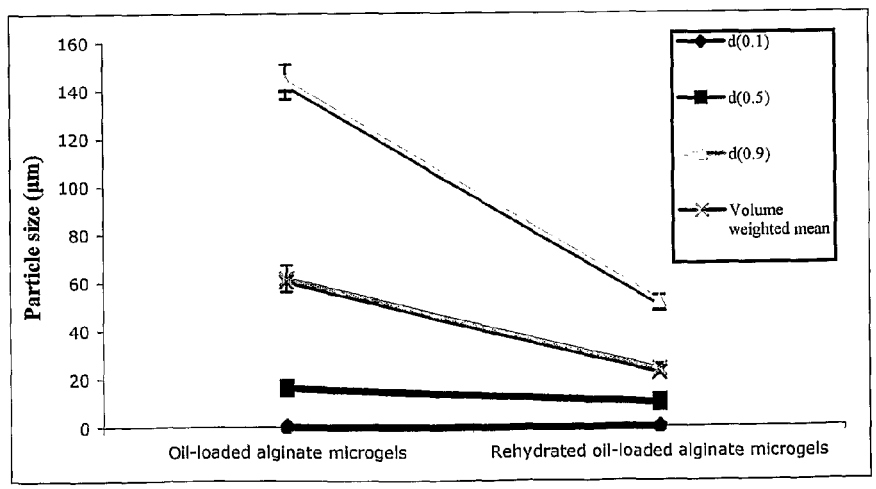
FIG. 23 Difference in size distribution between oil-loaded alginate microcapsules (suspended in water) and rehydrated spray dried microcapsule powder of similar composition.

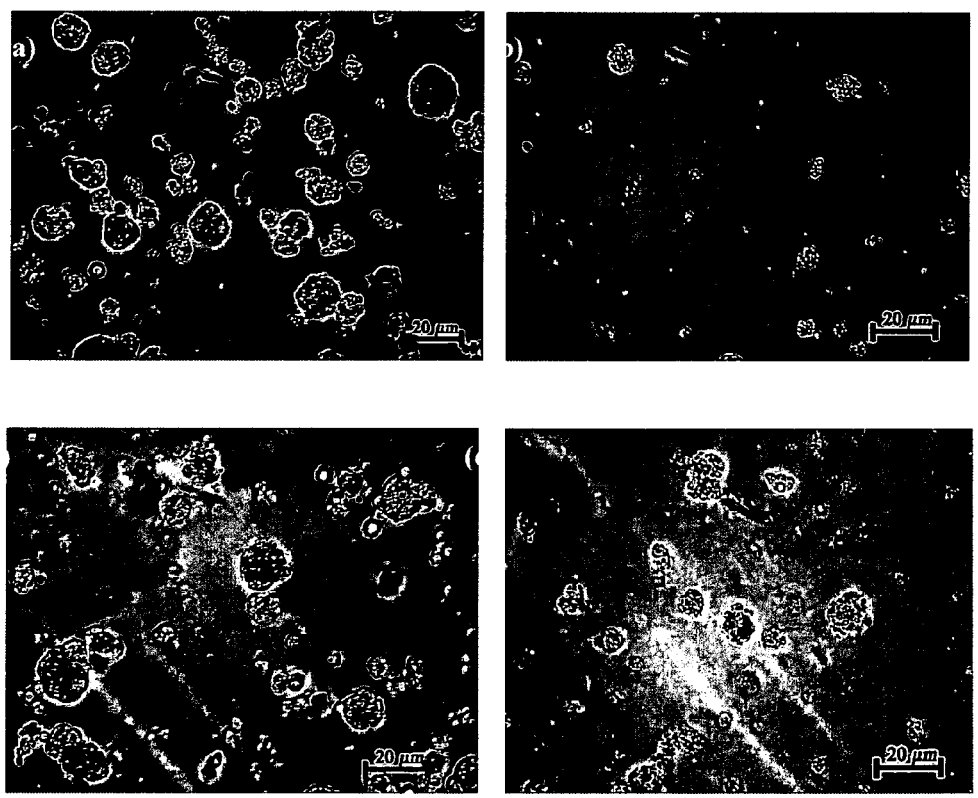
FIG. 24 Image analysis of fish oil-loaded alginate microcapsules. (a)(c): Microcapsules before spray drying (wet). (b)(d): Spray dried microcapsules rehydrated in water.

DEVICE AND METHOD FOR PREPARING MICROPARTICLES

FIELD OF THE INVENTION

The present invention generally relates to the field of microparticles and their preparation. For example, the invention relates to a devices and methods for the generation of microparticles, and also to microparticles prepared by those devices and methods.

The present invention also relates to microparticles including an active ingredient, to the preparation of such microparticles and to the use of such microparticles as a means of conveying and delivering an active ingredient.

BACKGROUND OF THE INVENTION

Microencapsulation is a process in which thin films or coatings or solid/gel matrix surround tiny particles or droplets that could be of any state of matter (solids, liquids or gases). Resultant sealed minicapsules are known as microcapsules or microspheres collectively termed as microparticles, which are typically spherical in shape and contain active material or core material surrounded by continuous wall or trapped in the solid or gel matrix. The active material that is encapsulated is known as the core, internal phase, fill, payload, or nucleus, whereas the material encapsulating is known as shell, coating, membrane, or wall material. Microcapsules may vary in size ranging from sub-micrometer to several millimeters. Typically, the average particle size is in the ranges from 5-300 micron in diameter. Most microcapsules have diameters between a few micrometers and a few millimeters.

The aim of microencapsulation is to provide a substance (active) in a finely divided state, to preserve it from degradation by limiting its exposure to the external environment (e.g. heat, moisture, acid, air, light) and to release it at a controlled rate under specific conditions on demand. It also helps the manufacturers cost effectiveness by having control of the optimal usage of the active. Further, by encapsulation volatile, sensitive, and reactive compounds can be turned into stable ingredients. Thus, microencapsulation itself not only is an added-value technique but also produces ingredients with numerous features. Moreover, masking the flavour of an active and providing uniform dispersion are also salient features of micro encapsulation.

Hydrocolloid micro-particles can be prepared, for example, by the emulsification method, or by the dripping method. One shortcoming of the emulsification method is that of residual organic solvent left in the microparticles, while the dripping method has been found to be unsuitable for scale-up and subsequent applications. Large-scale preparation methods for hydrocolloid particles, such as alginate particles, have been previously disclosed. However, residual organic solvent remaining in the microparticles is constantly a concern. An air-atomisation technique has been investigated to produce alginate-polylysine micro-capsules of Bacillus Calmette Guerin (BCG). This method is based on batch processing, of spraying sodium alginate into a calcium chloride bath, from which micro-gels are then separated.

A variety of techniques exist for microencapsulation of active ingredients. The techniques have associated benefits but also drawbacks.

For example, in spray drying material to be encapsulated is dissolved thoroughly with a carrier material (such as modified starch, maltodextrin, gum etc) and this solution is then fed into spray drier and atomised with a nozzle/spinning wheel. Hot air in the drier evaporates water and particles are collected at the bottom of the drier. Whilst an economical process, with this method there is a limited choice of coating material available, as mostly aqueous feed is used so that the resultant wall material is soluble in water. Heat can also cause degradation and/or oxidation of some active materials during drying and subsequent loss. Adherence of the core materials to the surface of the particles also increases the risk of oxidation. Spray dried capsules are water-soluble and therefore, the integrity of the capsules can be lost during rehydration.

Extrusion techniques can be used for volatile and unstable flavours in carbohydrate matrices. In this method carbohydrates, mixture of sucrose and maltodextrin are fed and melted by heat and sheared in an extruder so that crystalline structure is changed into amorphous form. Carbohydrates like sugar, starch hydrolysate are mostly used as encapsulating matrix. The encapsulant (active) is added through another opening at a cool side of the extruder near the extruder die. Core material dissolves in carbohydrate matrix and then forced through series of dies which enable its shape. The coating material hardens when it comes into contact with the liquid and causes encapsulation. This technique can provide excellent stability against oxidation and heat sensitive materials like *Lactobacillus acidophilus* can be encapsulated. However, extrusion methodology typically produces large particle size (500-1000 μm) which limits its sensory use. Moreover this method is expensive, sophisticated and complex to perform. Extruded granules may also show stickiness and clumping, and pay load concentrations can be low.

In co-crystallization, sucrose is used as a matrix for the coating and entrapment of a core material. Sucrose syrup is first concentrated to a super saturated state at high temperature (above 120° C.) and low moisture (95-97° Brix) to prevent crystallization. Active material is then added to the concentrated syrup with vigorous agiatation. As the temperature continuously increases, the syrup reaches a temperature where transformation and crystallization starts and heat is emitted. Encapsulated material is discharged and dried. In this approach the load of active material is generally very low and the process cannot be used for encapsulating heat sensitive materials.

Gel encapsulation involves the encapsulation of an active material in a gel (usually an alginate) matrix. The gel is formed by cross-linking of a polymer in which the core materials are suspended or dissolved. The microparticles can be formed by a variety of techniques including includes extrusion, emulsification, air atomization, electrostatic atomization, jet break-up, spinning disk atomization and by using a micro-nozzle array. However, none of these approaches is without practical difficulties as noted below.

Extrusion is a non-continuous process which tends to produce microparticles of only large size, and scale up can be problematic.

With the emulsification process, the gel particles produced have oil attached and removal of oil, or separation of oil from the aqueous phase of the gel particles, is required. This can be messy, difficult and time-consuming. The process is also not continuous.

With air atomization a coating material (e.g. sodium alginate) is extruded through a syringe pump into an air atomizer device and sprayed into a reagent bath (e.g. calcium chloride). Divalent calcium ions cross link the sodium alginate droplets and form microgel particles. Scaling up can be a problem as large number of beads cannot be formed due to limited interfacial surface of the calcium bath. It is a non-continuous method and there is difficulty in separating the beads.

In electrostatic atomization (electrospray or electrohydrodynamic atomization (EHDA)) electrified liquid is dispersed to fine droplets where electrostatic force is working on the charged surface of a liquid. Coating material is supplied to a nozzle electrode by using a micro syringe pump and dc high voltage is applied to the nozzle against an earth electrode. The droplets are dropped down into aqueous calcium chloride. It is a non-continuous method and has less scale up potential. It also tends to be a complicated operation.

The jet break-up approach is further divided into two methods, i.e vibration nozzle technology and jet-cutter technology. With the vibration nozzle method a suspension solution is forced through a small orifice. The liquid jet breaks into equally sized droplets by a superimposed vibration and solidified to form particles. Beads are produced that are spherical in shape with diameter range of 0.1-3.0 mm. This is a non-continuous method used only for small scale production of beads as beads are formed one after the other.

With jet cutter technology a fluid suspension is passed at high velocity through a nozzle in the form of a jet. The nozzle jet is cut into small pieces by rotating cutting wires. These cut at regular intervals forming same sized drops which are gelled in a bath of crosslinking reagent. Though the production rate can be increased by up to five fold when compared with the vibrating nozzle method, a still higher production rate would be preferred.

Spinning disk atomization is mostly used in biotechnology and medical fields. This technology permits production capacities from grams/min when using a single disc up to tons/day for a multi disk system. In this method alginate solution is delivered on the disk via a peristaltic pump with variable flow rates. Alginate droplets of desired sizes are collected in a $CaCl_2$ bath. This tends to be a non-continuous method.

Use of a micronozzle array involves feeding a coating solution (e.g. alginate) into a stream of oil (soybean oil) through a MN (micro-nozzle) array in an upper stream and a cross-linking agent ($CaCl_2$) through the downstream area of the oil from another MN array. The alginate and $CaCl_2$ droplets collide with one another in the oil and reaction takes place resulting in the form of gel particles. This tends to be a complex method and there is limited scale up potential.

With a Voretx-Bowl Disk Atomizer System coating material is fed onto a rotating disk through a distributor present at the center above the disk. A vortex bowl is attached to the top of the shaft. Gelation solution ($CaCl_2$) is fed to the centre of the bowl underneath the disk. All disks are rotating. Centrifugal force creates a wall along the inner side of the bowl. Alginate ejecting through the disk collides the wall and gel particles are formed and collected from a vat of $CaCl_2$. This process can be difficult to operate however.

The present invention seeks to provide a microgel encapsulation technique that does not suffer the drawbacks associated with the various techniques. Thus, the present invention seeks to provide a process that can be operated in a continuous manner and that is cheap and easy to operate. The present invention also seeks to provide a process that can produce a small size microparticle (for example of less than 50 μm) and that lends itself to scale up for microparticle production.

SUMMARY OF THE INVENTION

Accordingly, in one embodiment the invention provides a method for preparing microparticles comprising mixing a first cross-linkable reagent in aerosol form with a second cross-linking reagent in aerosol form to thereby form microparticles.

In accordance with the present invention it has been found advantageous to produce microparticles by contacting (and reacting) respective aerosols comprising mutually reactive reagents.

In another embodiment the invention provides a reactor suitable for implementing the method of the invention, the reactor comprising a reaction chamber comprising a first atomiser for introducing an aerosol of a cross-linkable reagent into the reaction chamber, and a second atomiser for introducing an aerosol of a cross-linking reagent into the reaction chamber.

The first and second atomisers are arranged within the reaction chamber so that aerosols produced by the respective atomisers can be caused to impinge on each other thereby facilitating contact (and reaction) between the cross-linkable and cross-linking reagents used.

Formation of the microparticles in accordance with the present invention actually takes place when the aerosols contact each other, i.e. within the body of the reaction chamber, and formation of the microparticles is not contingent upon contact of precursor particles with some other reagent. In this regard the present invention should be contrasted with those conventional techniques that form pre-cursor particles which are then delivered into a bath/vat including a further reactant for reaction with the pre-cursor particles to form the intended microparticles.

The method of the present invention may also be applied to produce microparticles incorporating an active ingredient (active). As will be described, the active may be incorporated into the microparticles during their production. Alternatively, or additionally, the active may be incorporated into the microparticles after they have been produced.

In a further aspect the invention provides microparticles produced in accordance with the method of the present invention.

Other aspects of the present invention will become apparent from the following detailed discussion.

DETAILED DISCUSSION OF THE INVENTION

Central to the present invention is the production of aerosols of reactive components, with contacting of the aerosols leading to production of microparticles. One aerosol includes a cross-linkable reagent and the other aerosol includes a reagent that will effect cross-linking of the cross-linkable reagent when the two reagents come into contact. Cross-linking typically occurs under the prevailing conditions at which contacting of the aerosols takes place, although this is not essential, and a change in ambient conditions after mixing of the reagents could be used to initiate cross linking. The reactants will be selected so that the rate of reaction is suitably high under the prevailing conditions so as to form coherent and discrete microparticles. Elevated temperature and/or pressure may however be adopted. As noted, in the methodology of the present invention the microparticles are formed when the aerosols contact each other, rather than subsequently involving some further reagent. Thus, in accordance with the present invention, it is not subsequently necessary to immerse the particles in a further bath of a reagent. The approach adopted in the present invention has a number of associated advantages as follows.

It provides greater control over exposure of reagents thereby allowing highly controllable and uniform yield (assuming reagent concentration in respective aerosols remains constant). Immersion of microparticles in a reagent bath/vat can lead to non-uniformity and product contamination.

It allows control of microparticle size, including production of small particle sizes (<40 μm) by suitable control of aerosol droplet sizes.

Depending upon reagents the approach is operable at room temperature (though elevated temperature may be employed to influence viscosity of reagents and sol-gel transition rate).

Avoids possible contamination with (organic) carrier streams.

In general terms the reagents present in respective aerosols are referred to as cross-linkable and cross-linking reagents. Therein the term "cross-link" (and variations thereof), generally refers to a chemical link between two or more polymeric chains of atoms. Generally, the cross-linkable reagent is a molecule, typically a polymer incorporating repeat units, that includes groups or moieties that can be cross-linked. Cross-links bind molecules together into a network, forming a larger molecular superstructure. The cross-links may be ionic, dative, complexation and coordination linkages, covalent, and may also involve hydrogen-bonding interactions. Thus, an ionically cross-linkable polymer, therefore, is generally a polymeric molecule that is capable of forming cross-links by reaction with an ionically cross-linking reagent so as to form microparticles. Ionic cross-links may be reversible or irreversible. An ionically cross-linkable reagent has one or more ionisable groups. The term "ionisable group" refers to a chemical moiety capable of partial or full ionisation.

The cross-linkable reagent may be a basic polyelectrolyte (poly base), basic ionomer, acidic polyelectrolyte (poly acid), or an acidic ionomer. In some embodiments, the crosslinkable reagent is selected from one or more anionic monomers or polycations. As used herein, the term "polycation" or related terms such as "cationic polymer" refer to a polymer composed of positively charged macromolecules. In some embodiments, the cross-linkable reagent is selected from one or more anionic monomers or polyanions.

Suitable cross-linkable polymers may be selected from the class of hydrogels include hydrocolloids. Hydrocolloids are hydrophilic polymers, of vegetable, animal, microbial or synthetic origin, that generally contain many hydroxyl groups and may be polyelectrolytes. Hydrocolloid which are not ionically cross-linkable may be used in blends with polymers which are ionically cross-linkable.

Polymers which may be used in the present invention include but are not limited to one or a mixture of polymers selected from the group consisting of polyvinyl alcohol, alginates, carrageens, pectins, carboxy methyl cellulose, hyaluronates, heparins, heparin sulfates, heparans, chitosans, carboxymethyl chitosan, agar, gum arabic, pullulan, gellan, xanthan, tragacanth, carboxymethyl starch, carboxymethyl dextran, chondroitins including chondroitin sulfate, dermatans, cationic guar and locust bean, konjac, gum ghatti, xyloglucans, karaya gums, cationic starch as well as salts and esters thereof.

Exemplary anionic polymers include one or a mixture of alginates acid, pectins, carboxymethyl cellulose, hyaluronates. Exemplary cationic polymers include chitosan, cationic guar, and cationic starch.

The ionically cross-linkable polymers from which the microparticles of this invention may be generated may be functionalised with carboxylic, sulfate, phosphate, sulphonamido, phosphonamido, hydroxy and amine functional groups.

In a preferred embodiment of the present invention formation of the microparticles takes place by a sol-gel phase transition and the reagents used in this embodiment should be understood accordingly. Thus, in principle the cross-linkable reagent and cross-linking reagent may be selected from any suitable combination that will result in formation of microparticles in accordance with the methodology of the present invention by a sol-gel phase transition associated with the cross-linkable reagent. This said, other factors may influence selection of reagents, including the intended end use of the microparticles. For example, if the microparticles are intended for human or animal consumption, they must be physiologically acceptable. The compactability of the reagents with actives, and the release characteristics of such actives when present in the microparticles will also need to be considered.

This preferred embodiment of the present invention will be described for the purposes of (non-limiting) illustration with reference to the use of alginates as the cross-linkable reagent. Alginates are particularly preferred for use in the method of the invention because they are physiologically acceptable and they form thermally stable gels after binding with a suitable cation. Ionic gelation of alginates is based on their affinity towards and ability to bind certain ions. Alginates form strong, stable gels with divalent cations such as $Ca^{2+}$, $Sr^{2+}$, $Zn^{2+}$, $Co^{2+}$ and $Ba^{2+}$. Trivalent cations, such as $Fe^{3+}$ and $Al^{3+}$, may also effect gelling. There is no gelation with monovalent cations.

The use of alginate gels in the present invention is also advantageous since these gels exhibit desirable active release characteristics. For example, alginate gels show stability as low pH conditions as they shrink and do not swell and disintegrate. Active release is therefore also low. On the other hand alginate gels swell rapidly and show dissolution and/or disintegration in weak alkaline conditions. This property enables alginate gels to be used effectively to deliver drugs to the human intestine (pH above 6.7). Alginate gels are also mucoadhesive and tend to stick to the intestinal mucosa for prolonged periods.

A number of factors influence alginate gel formation and these may need to be considered when implementing the present invention. One factor is the prevalence and length of gluconate (G) residues against the prevalence and length of mannuronate (M) residues. The M/G ratio is an important factor, at least in relation to $Ca^{2+}$ cross-linking. As the M/G ratio decreases, the requirement for $Ca^{2+}$ ion concentration increases for effective cross-linking. Gels formed from alginates with a high G content also tend to be stiffer, more brittle, and more porous and maintain strength and integrity for longer periods of time. Such gels do not swell excessively on cross-linking. Alginates with a high M content tend to form softer, less porous elastic gels with high shrinkage. Such gels swell more, dissolve more easily and increase in size more than high G content alginate gels. The gel strength also increases with increase in alginate concentration and with high G content.

With reference to using $CaCl_2$ as cross-linking reagent, gel strength increases with $CaCl_2$ concentration up to about 0.02M. Above that concentration gel strength remains essentially constant.

One benefit associated with the use of alginates is that the gels thermal uses are stable independent of temperature (upto the boiling point of water). However, the kinetics of gelling can be modified by adjusting the prevailing temperature as might be necessary.

These factors, and others, may be manipulated to achieve the desired outcomes with respect to gel formation and gel properties. These kinds of factors will also need to be considered using other types of cross-linkable and cross-linking reagents.

Although alginates may be preferred in practice of the present invention other combinations of cross-linkable reagent and cross-linking reagent may be used including chitosan+tripolyphosphate, carboxymethylcellulose+$Al^{3+}$, k-carrageen an and $K^+$, k-carrageen+$NH_4^+$, pectin+$Ca^{2+}$, gelan gum+$Ca^{2+}$, polyphosphazene+$Ca^{2+}$.

The reaction chamber used in the present invention includes at least two atomisers for formation of the aerosols of respective reagents. Typically, the atomisers are arranged facing each other in a cylindrical chamber (for containment of the aerosols and microparticle products). This arrangement of atomisers is intended to achieve impact and intimate mixing of the two aerosols. Generally, each atomiser will have the same general structure but this is not mandatory. Each atomiser typically produces a spray angle of approximately 20°.

The term "atomiser" as used herein is intended to denote any device that may be used to provide an aerosol (mist) of reagent. The process of atomisation can be understood as the separation of something into fine particles, such as the reduction of a liquid to a very fine spray or mist. The mist of the cross linking agent can be generated in a separate chamber and supplied to the reaction chamber. Atomisation of a solid or liquid provides a collection of smaller particles that are suspended in an atmosphere/vehicle that is used to form/fluidise the particles. Typically, this atmosphere/vehicle is a gas or mixture of gases. The gas may be air or an inert gas such as helium, argon or nitrogen. In the context of the invention an aerosol can therefore be regarded as being any suspension of solid and/or liquid particles in a gas.

Desirably, the reagents used to form the aerosols are both in liquid form. This allows ease of implementation and control of aerosol droplet size. One or both reagents may exist as liquids or they may need to be solubilised in a suitable solvent. It may be necessary to modify the viscosity of reagent solutions in order to effect aerosol formation as desired.

The aerosols can be generated by a variety of techniques and atomisers. Atomisers for use in the invention include those that rely on centrifugal, kinetic, pressure or sonic energy. Preferred atomisers include pneumatic and ultrasonic atomisers. One skilled in the art will be familiar with construction and operation of such devices in order to achieve the desired production of aerosols having suitable droplet size, density and/or distribution. These and other factors are likely to influence production of microparticles. Thus, it may be necessary to manipulate a variety of process parameters in order to produce aerosols that will yield microparticles having desired characteristics.

An active may be incorporated into microparticles in accordance with the present invention in a number of ways. Firstly, the active may be incorporated into the microparticles as they are produced. In this case the active is typically provided in solution with the cross-linkable reagent, or as a suspension of particles of the active in a solution of the cross-linkable reagent, so that the aerosol produced comprises droplets including a combination of active and reagent. It is also possible for the cross-linkable reagent and active to be provided in the form of an emulsion, where the two are immiscible. In that a suitable surfactant may be required to maintain emulsion stability, although this may not be essential if the emulsion is formed just prior to aerosol formation and if the gelling reaction is suitably rapid so as to maintain distribution of the active in the cross-linkable reagent, or vice versa. Additionally, or alternatively, the active may be provided in solution with the cross-linking reagent, or as a suspension of particles of the active in a solution of the cross-linking reagent, so that the aerosol produced comprises droplets including a combination of active and reagent. It is also possible for the cross-linking reagent and active to be provided in the form of an emulsion, where the two are immiscible.

In another embodiment the active may be incorporated into the microparticles after the microparticles have been formed. In this case the microparticles may be exposed (immersed) in a solution of active with molecules of the active permeating the microparticulate structure. The actives may be hydrophilic, hydrophobic or in water insoluble particulate form.

In all cases the concentration of active may be adjusted as necessary based upon a variety of factors including the microparticle size, the dosage regime required and/or the release characteristics of the active in the as-formed microparticle.

Release of active from the microparticles may be via a diffusion mechanism with molecules of the active migrating through the permeable gel membrane/matrix of the microparticles. This process is highly dependent upon the pore size of the gel phase of the microparticle. In the case of an alginate gel, increasing the relative concentration of alginate (matrix) decreases the rate of diffusion of actives. As noted earlier alginate gels having a high content of G residues are more porous and tend to promote diffusion. The coating thickness of the gel will also influence release rate. Environmental conditions will also influence release rate. The local pH to which the microparticles are exposed may be influential here.

Additionally, or alternatively, release of active may also occur as a result of erosion, dissolution and/or degradation of the gel making up the microparticle. Leaching of cations e.g. $Ca^{2+}$, may cause these effects to occur.

The active may be selected from a variety of functional substrates that are conventionally provided in microencapsulated form for consumption or other use as might be necessary. Such actives include:

probiotics, such as *lactobacillus acidophilus, lactobacillus plantarum*, and animal feed supplements;

micro-organisms;

viruses;

oils, such as fish oils e.g. (omega-3);

pharmaceuticals, such as ibuprofen and gentamicin;

enzymes, such as lysozymes and insulin;

vitamins, such as vitamins A, E, D, K1, B12, B9, B1 and B6;

cosmeceuticals, such as personal care products e.g. fragrances, deodorants, insect repellents;

dies or inks (for use in printing); and agricultural activities such as pesticides, herbicides and fungicides.

In relation to such actives the present methodology provides a low cost, scalable microencapsulation process to produce controlled release microparticles. Microencapsulation may also be used to mask the taste and/or smell of an active and to provide a convenient form in which the active is available for use.

Once formed the microparticles may be separated using known techniques and devices, including centrifugal separators, clarifiers, membrane filtration and filter presses depending upon the product encapsulated, microparticle size and specific gravity. If the actives are not heat sensitive, heat may be applied to cause syneresis of the gel in order to facilitate removal of water. The microparticles may then be spray dried or freeze dried with or without the presence of other carrier solids (such as maltodextrins, sugars) as necessary to provide robustness.

If the microparticles have been formed with active incorporated they may be in a form ready for use or added to another product as necessary. For example, when the active is a probiotic the microparticles may be incorporated in a food or drink product, such as yogurt and fruit juice. Of course, the microparticles must be inherently suitable for such use and any trace reagents may need to be washed from the microparticles before they are used. For example, when $CaCl_2$ is used to effect getting of an alginate, the microparticles may need to be washed to remove unused $CaCl_2$. If the microparticles do not contain active, they may be processed so as to impregnate them with a suitable quantity of active.

Microparticles produced in accordance with the present invention may be coated with cross-linkable reagent and contacted with further cross-linking agent so as to develop a multi-layer or thicker coating on the microparticles. The same general philosophy as described herein may be adopted although formation of aerosol of the coated microparticles may necessitate a different approach from that used initially to form the microparticles. This process may be repeated, for example up to 50 times, in order to develop a microparticle size and structure. The coating(s) that is/are subsequently applied may be formed from the same or different cross-linkable reagent that is used to form the original microparticle. Each coating may include no active or an active that is the same or different (in type or concentration) from an active previously incorporated in the microparticles. This embodiment therefore allows great flexibility with respect to microparticle design, functionality and release characteristics.

By way of example, alginate beads (microparticles—negatively charged) may be coated with chitosan (positively charged) by submerging the alginate beads in a chitosan solution. The chitosan naturally aggregates on the surface of the alginate beads. In this way layers with different properties can be produced. The experimental procedure for applying a chitosan layer to alginate particles may be as follows. A 1% chitosan solution is prepared in 1% acetic acid solution. This solution is poured into a preformed alginate bead suspension at alginate:chitosan solid ratios of 10:0.01 to 10:0.2. The ratios can be varied based on the size of the particles and the thickness of the outer layer desired. The coating is found to harden the gel particles. The lower concentration ratio of chitosan produces softer gel particles than the higher concentration. The chitosan may also be mixed with the cross-linker ($CaCl_2$) solution, thus the mist of cross-linker may contain chitosan. The microgel particles obtained may be a bit sticky in nature and agglomerates of primary particles may be obtained. The agglomerates can easily be broken by simple agitation, however.

The present invention also provides a method of delivering an active by incorporating the active in a microparticle in accordance with the method of the invention s described herein. The active may be intended for consumption or microencapsulation may simply provide a convenient means of providing the active for end use.

Preferred embodiments of the invention will be described with reference to the accompanying drawings in which:

FIG. 3 shows a photographic representation of the reactor;

FIG. 6 shows a photographic representation along side a graphical representation of the reactor;

FIGS. 12 to 15, 18 to 20, 22 and 23 represent graphically experimental results discussed herein;

FIGS. 16, 17 and 24 show the morphology of microparticles in accordance with the present invention; and FIG. 21 illustrates microparticles in accordance with the present invention.

Figure 1:
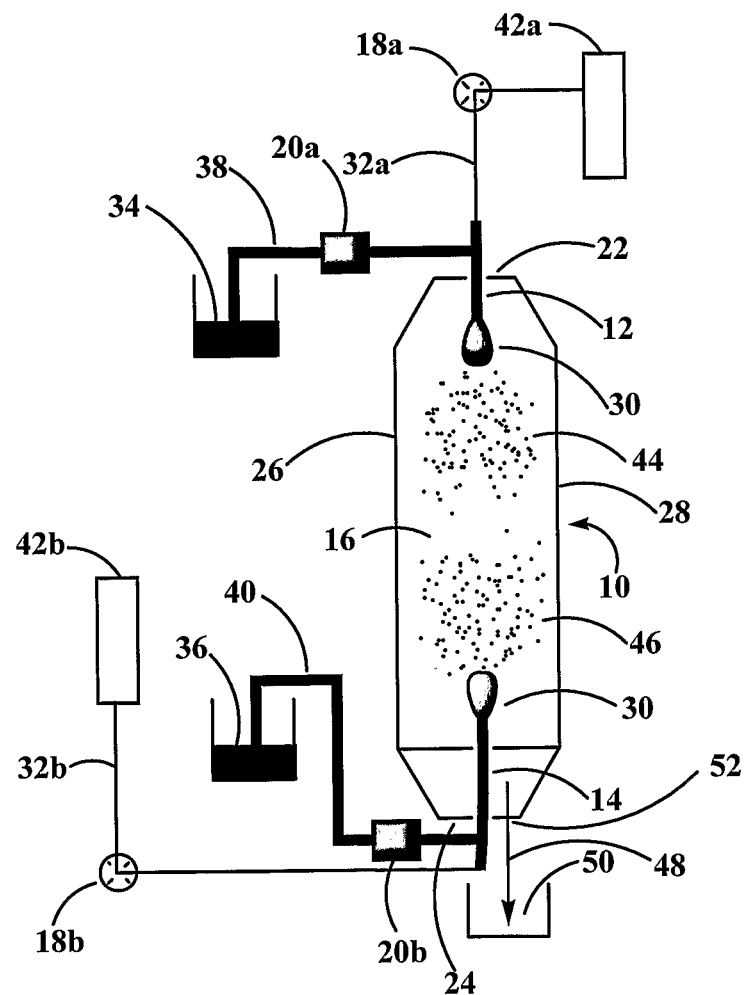
FIG. 1 shows cross-sectional view of the reactor of one embodiment.

Referring to the drawings it will be appreciated that the invention may be implemented in various forms, and that this description is given by way of example only.

Referring to FIG. 1, the reactor (10) is usually comprised of the following four major components: atomisers (12 and 14); reaction chamber (16); pressure regulators (18a and 18b) and feed pumps (20a and 20b). The first atomiser (12) is used to generate an aerosol (44) of a first reagent (34)—being in the form of a cross-linkable reagent. The second atomiser (14) is used to generate an aerosol (46) of a second reagent (36)—being in the form of a cross-linking reagent.

Each of the atomisers (12) and (14) typically includes a reservoir of reagent (34), (36), which is coupled via a respective reagent feed line (38), (40), to one or more atomiser nozzles (30). The feed pumps (20a), (20b) are provided in each of the feed lines (38), (40) allowing the supply of reagent to be controlled. The atomisers also (12), (14) also typically include a fluid supply (42a), (42b) for supplying a flow of fluid via fluid feed lines (32a), (32b). The fluid is used in atomising the reagents, as will be described in more detail below, and could therefore be any form of suitable fluid, such as air, nitrogen, or the like. Again, the pressure regulators (18a), (18b) may be provided for adjusting the flow pressure of the fluid.

In use, fluid from each of the fluid supplies is urged through the fluid feed lines (32a), (32b) and mixed with reagent supplied via the reagent feed lines (38), (40), before the mixture is supplied to the atomisers (12), (14). During this process, the relative ratios of the fluid and the reagent can be varied by altering the fluid flow pressure and through use of the control valves (20a), (20b), allowing the relative concentration of reagent in the aerosols (42), (44) to be controlled.

The atomisers generate the respective aerosols (44), (46), which then mix within the reaction chamber (10). In general, the aerosol droplets are charged, causing droplets of first and second reagents to contact, thereby causing initiation of the cross linking process, thereby forming the microparticles. As the microparticles form, they drop to the bottom of the reaction chamber (24), and are removed via an aperture (52), allowing the microparticles to be collected in a collection chamber (50), as shown by the arrow (48). At this point the microparticles can be separated from any unreacted reagents, for example through filtering or the like, as previously described.

Figure 2:
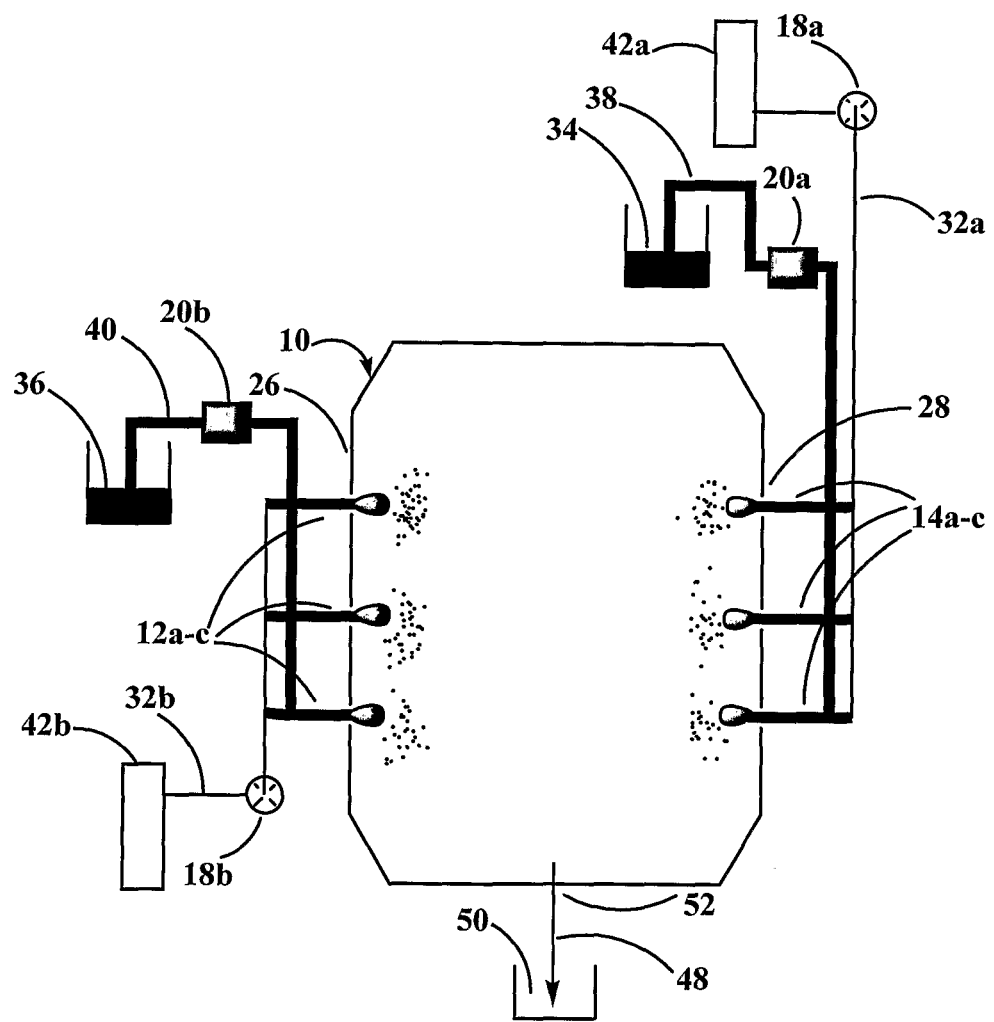
FIG. 2 shows cross-sectional view of the reactor of another embodiment.
Figure 4:
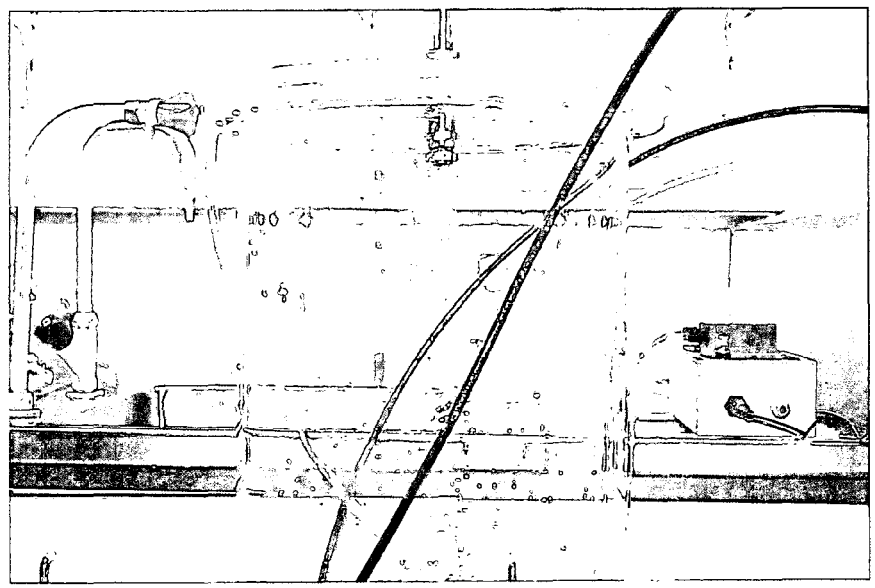
FIG. 4 shows a photographic representation of the top of the reactor of FIG. 1.

Each atomiser (12), (14) may individually constitute a plurality, or an array, of atomisers. For example, as shown in FIG. 2, the first reagent may be sprayed into the reaction chamber by three separate atomisers (12a-c), and the second reagent by a further three separate atomisers (14a-c). Alternatively, for example, there may be two atomisers for the first reagent, and one atomiser for the second reagent (not shown). Atomisers may be located at opposing ends of the reaction chamber such as at the top (22) and bottom (24) of the reaction chamber (26) as shown in FIG. 1. Alternatively, the atomisers may be located along the sides (26) and (28) of the reaction chamber (26) as shown in FIG. 2.

Other possible variations in the number and position of atomisers will be known to those skilled in the art. Thus, for example, the atomiser (12) for creating the aerosol of the first reagent could be provided at the top (22) of the reaction chamber (26), so that the first reagent falls under the influence of gravity. One or more second atomisers (14) can then be provided on sides (26), (28) of the reaction chamber (10), thereby forming a layer of aerosol (46) in a mid portion of the reaction chamber (10). This allows the first reagent aerosol (44) to fall through the layer of the second reagent aerosol (46), thereby allowing mixing of the reagents to take place. In this example, by controlling the thickness of the layer of the second aerosol (46), this can be used to control the duration for which the first reagent is exposed to the second reagent, thereby providing control over the cross linking process. In general the layer would be at least 10 mm thick, although any suitable thickness could be used depending on the reagents used. The aerosol of the crosslinking agent can be generated in a separate chamber and supplied the reaction chamber.

As mentioned above, atomisation may be accomplished by use of a nozzle (30). A nozzle is a mechanical device designed to control the characteristics of a fluid flow as it exits from an enclosed chamber into some medium, for example, air, nitrogen or argon. Frequently, the purpose of a nozzle is to increase the kinetic energy of the flowing medium at the expense of its pressure energy. A nozzle is generally a pipe or tube of varying diameter, and it can also be used to direct or modify the flow of a liquid or gas. However, it will be appreciated that any suitable technique of generating aerosols (42), (44) could be used, such as injecting fluid to into a low pressure environment, dropping reagents onto a rotating disc, or the like.

The reaction of the first and second reagents to form micro-particles takes place within the reaction chamber (16). The atomisation trajectory (e.g. direction of the spray), reaction time and volume of the product to be processed influences the diameter and length of the chamber (26). The reaction chamber may be, therefore, of various in shapes and sizes. The reaction chamber may be elongate, cylindrical, squat, rectangular, hexagonal & etc. The cylindrical nature of the reaction chamber (16) of one embodiment, can be seen in the photographic representation of FIG. 3. Suitably, the internal volume of the reaction chamber can be increased or decreased.

If required, the internal temperature of the reaction chamber may be reduced or increased by refrigeration or heating means. This can be used, for example, to control the ambient conditions to which the reagents are exposed after mixing, thereby influencing the cross linking process. This can be useful for ensuring complete cross linking before the resulting microparticles are extracted from the reaction chamber (10).

Alternatively, or additionally, the reagent feed lines (38 and 40) may be subjected to heating or cooling to increase or reduce the temperature of the reagent prior to its introduction into the reaction chamber. This can also be used to modify the viscosity, surface tension or other properties of the reagents prior to formation of the aerosols (44), (46), which can assist in aerosol formation, as well as mixing of the resulting aerosols.

The reaction chamber may be sealed, and as such, the internal pressure of the reaction chamber can be reduced or increased. The reagents (34) and (36) may be introduced to the reaction chamber in any order, either sequentially or simultaneously.

Figure 3:
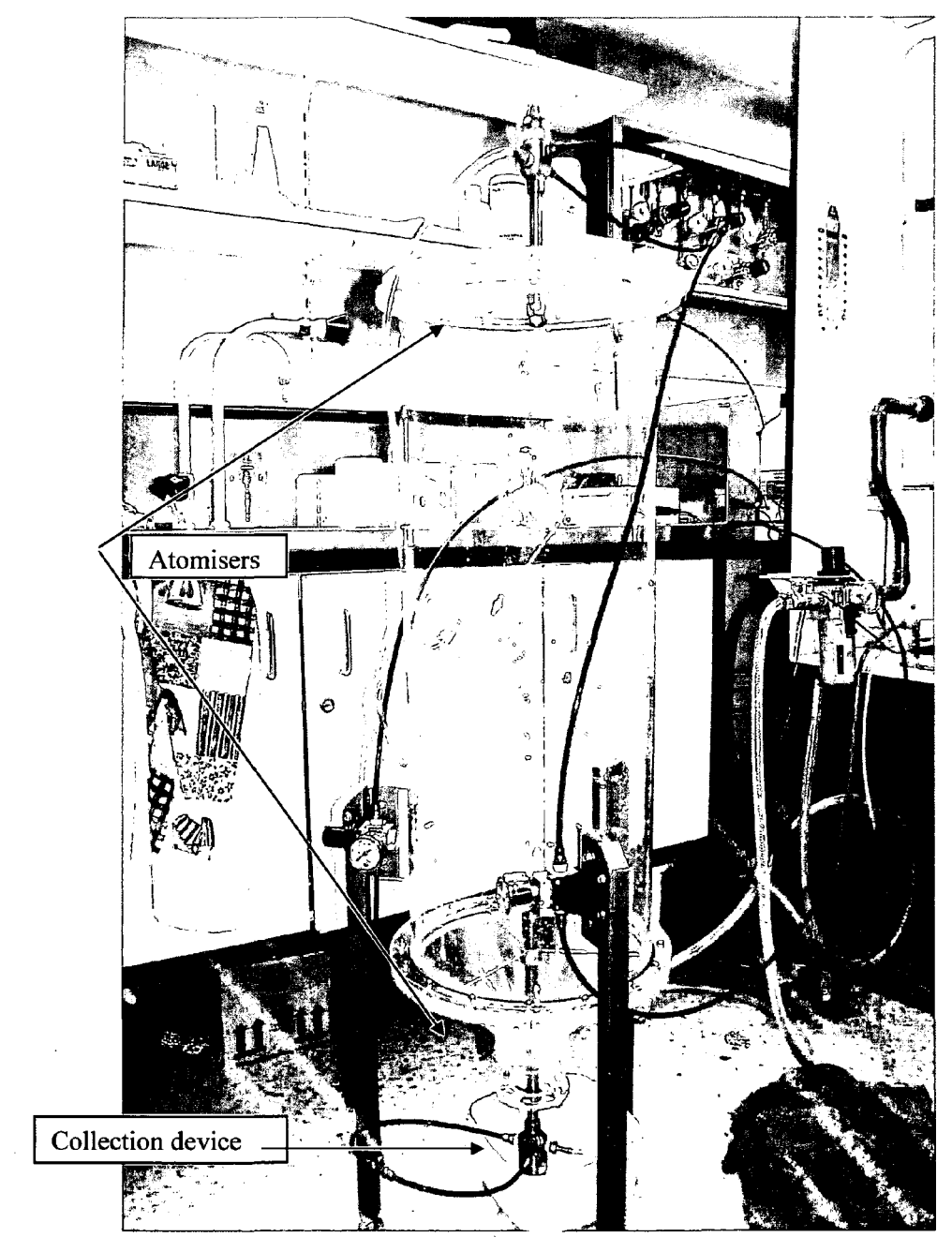
Figure 7:
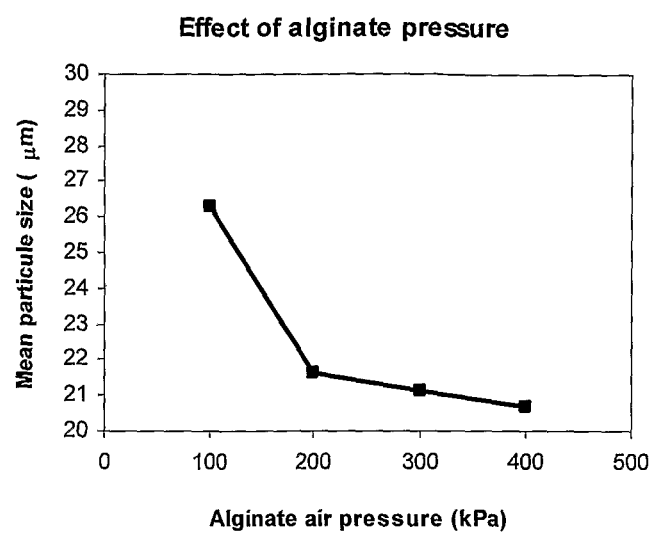
FIG. 7 represents graphically the effect on particles size of varying the air pressure of an alginate feed solution.
Figure 8:
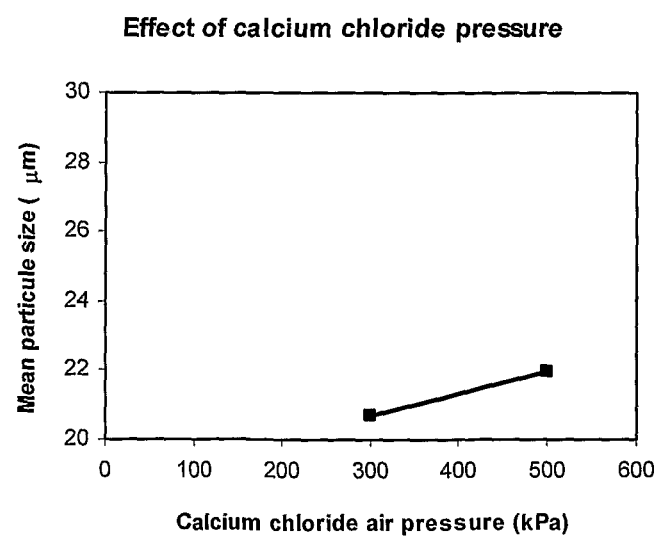
FIG. 8 represents graphically the effect on particles size of varying the air pressure of a $CaCl_2$ feed solution.

In the embodiment shown in the photographic representation of FIG. 3, the type of atomisers used is two-fluid nozzles where air is used as an atomising agent. The droplet size and distribution can be controlled by controlling the air pressure within the limit of the atomiser's capability. It is also possible to use other types of atomisers (such as nozzle or rotary type). The design of reactor chamber (26) can be varied based on the type of atomiser used. Through use of the pressure regulators (18a) and (18b), the pressure of the reagent passing through the nozzle head can be increased or decreased. The flow rate of the reagent through the nozzle head can also be increased or decreased. The effect of varying the pressure of the reagents can be seen in the graphical representations shown in FIGS. 7 and 8. The effect of varying the pressure of reagent 1, in this case a cross-linkable reagent can be seen in FIG. 7, the effect of varying the pressure of reagent 2, in this case a gelling agent which is a cross linking reagent, can be seen in FIG. 8.

Figure 9:
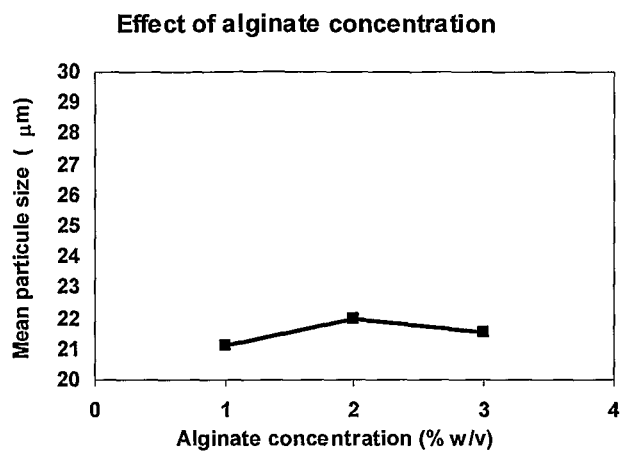
FIG. 9 represents graphically the effect on particles size of varying the concentration of an alginate feed solution.
Figure 10:
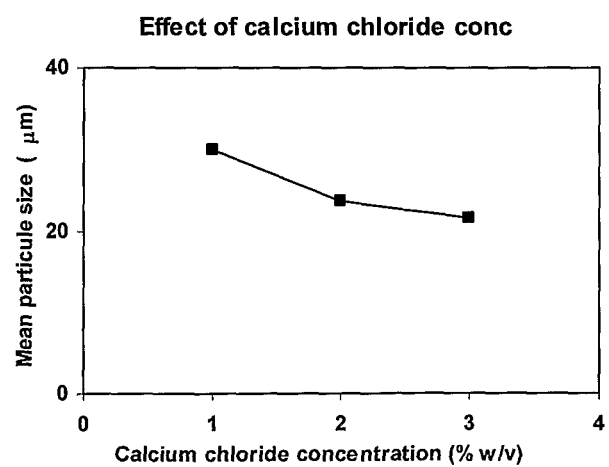
FIG. 10 represents graphically the effect on particles size of varying the concentration of a $CaCl_2$ feed solution.
Figure 11A:
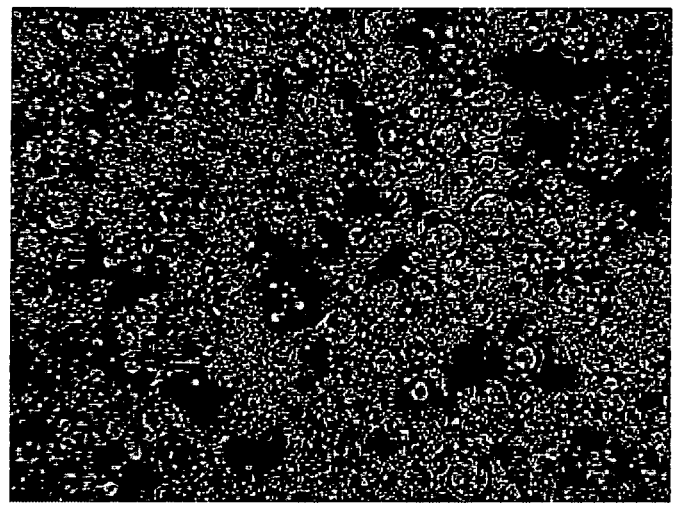
FIGS. 11a and 11b show image analyses of unclassified microparticles.
Figure 11B:
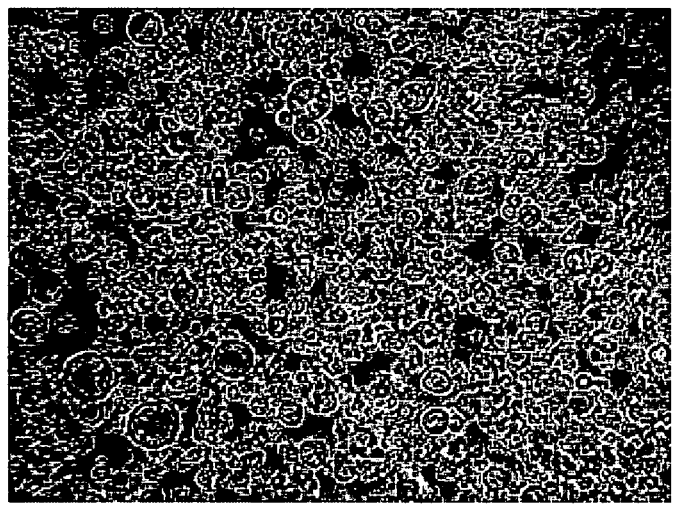

Referring to FIG. 1, both fluid reagents (34) and (36) are pumped through the reagent fluid lines (38) and (40) respectively by individual feed pumps (20a) and (20b). The type of feed pump can be for example, peristaltic, mono- or gear pump. The concentration of the reagents in the feed solutions (34) and (36) may be varied. The effects of varying the concentration of a cross-linkable reagent (alginate) and a cross-linking reagent ($CaCl_2$) in solution, can be seen by the respective graphical representations of FIG. 9 and FIG. 10.

It will be appreciated that the use of a reaction chamber in this fashion is for the purpose of example only, and it not necessarily required. However, the use of the reaction chamber can assist in controlling the ambient conditions under which the cross linking is performed, can help reduce contamination of either the reagents, or the resulting micro-particles, and can assist in containing the micro-particles to assist with collection.

In the above examples, the aerosols of the first and second reagents are formed using atomisers. However, any technique for forming aerosols may be used. Thus, for example, either one or both of the reagents could be formed as a mist within the chamber, and this could be achieved in any suitable manner, such as introducing reagents into a low pressure environment, to thereby induce droplet formation.

Additionally, the reaction chamber may be used to provide additional control over the micro-particle formation process, for example by providing different ambient conditions within the chamber to aid the mixing and cross linking processes. Thus, for example, the reagents could be mixed under ambient conditions in a first part of the reaction chamber. As the aerosols mix, droplets form which then fall towards a second part of the chamber, in which the conditions are modified, for example by heating or cooling, which could be used to initiate or aid the cross linking process.

The second reagent is generally a liquid solution of a gelling agent that induces a component of the first reagent to gel to form a microparticle. A gelling reagent may be a cross-linking reagent such as a solution of an inorganic salt. Generally, suitable cross-linking reagents are solution of dissolved ions. The cross-linking ions used to cross-link the first reagent may be anions or cations depending on whether the first reagent is anionically or cationically cross-linkable. Appropriate bio-compatible cross-linking ions include but are not limited to cations selected from the group consisting of calcium, magnesium, barium, strontium, zinc, boron, beryllium, aluminium, iron, copper, cobalt, nickel, lead and silver ions, or mixtures of any 2 or more thereof. Anions may be selected from but are not limited to the group consisting of carboxylate, phosphate, sulphate, oxalate, bicarbonate, and carbonate ions. More broadly, the anions are derived from polybasic organic or inorganic acids. Preferred cross-linking cations are calcium ions.

Alginates are sourced from processed seaweeds. The use of alginates in pharmaceutical and medicinal industries is driven by ongoing developments in controlled release technologies and the use of alginates in wound-care applications. Sodium alginate is also widely used as a binder and a disintegrating agent in tablets, as a suspending and thickening agent in water-miscible gels, lotions and creams, and as a stabiliser for emulsions. A potential application for alginates lies in the development of controlled delivery systems. The application of alginate in oral dosage forms with systemic effect is mainly based on alginate microparticles from which the release of incorporated drug is controlled by diffusion mechanism. The combination of alginate with multivalent cations, such as calcium, can form mechanically stable, ionically crosslinked microencapsules. Alginates may be used for the micro-encapsulation, immuno-isolation, and immobilisation of cells.

Micro-encapsulation may be used to deliver a host of substrates and ingredients such as—flavours, oils, active pharmaceuticals, peptides, biotics including probiotics, enzymes, milk proteins and protein concentrates, oligosaccharides, amino acids, enzymes, acidulants, colours and sweeteners—in a range of food and medicinal formulations, in the form of micro-capsules. The process of micro-encapsulation refers to a variety of processes, which are used to entrap an additive into a matrix material, such as a colloidal polymer particle. The additive may form a core covered by a shell, or may be dispersed throughout the polymer matrix. For example, microencapsulation may refer to process or technology by which thin coatings can be applied reproducibly to small particles or dispersions, thereby forming microcapsules. Microencapsulation has been use in the preparation of sustained release dosage forms. Generally, therefore, the term microcapsules refers to microparticles that contain an active agent or core material surrounded by a shell or coating, and are now increasingly being used in food ingredients preparation. The encapsulation efficiency, defined as a percentage of substrate component entrapped into the microcapsules, may vary depending on the substrate that is to be encapsulated.

Substrates to be encapsulated, but which do not participate in the cross-linking reaction, may also be added in aerosol form through the use of additional atomisers dedicated to introducing these substances into the reaction chamber (not shown). In such a way substrates, such as medicines or probiotics, can be incorporated or encapsulated into the micro-particles to form microcapsules. Other substrates, whether biological or chemical, can be encapsulated by solvating the substrate in one of the feed solutions (34) or (36). As such, the substrate is introduced into the reaction chamber along with the cross-linkable reagent and is encapsulated into microparticles, which form when the aerosol droplets containing the cross-linking reagent and the cross-linkable reagent collide and react. The aerosol streams will generally have smaller droplet sizes than the micro-particles formed.

The resulting microcapsules, for example, may be in the form of bioadhesive microcapsules, which permit the sustained release of active agents such as therapeutic or cosmetic agents into the digestive system or oral cavity.

The following non-limiting examples illustrate embodiments of the present invention.

Example 1

Preparation of Sodium Alginate and Calcium Chloride Solutions

Sodium Alginate solutions of concentrations 1-3% (w/w) were prepared in deionised water. Before reacting with $CaCl_2$, methylene blue was added to alginate solutions to enable viewing of the formed microgel particles.

The $CaCl_2$ solutions were prepared at the concentrations of 1-3% (w/v) in deionised water. The Calcium chloride solutions were reacted with the Na-alginate solutions randomly by varying the Na-alginate flow rate and the pressure.

Atomisation and Microgel Recovery

Sodium alginate solution was fed and atomised from the top nozzle, whereas $CaCl_2$ solution was atomised from the bottom nozzle. The experiments were carried out with the top nozzle at the air pressures of 20, 50 and 80 psi while the alginate flow rates at the top nozzle were maintained at 8, 16 and 24 mL/min. The $CaCl_2$ flow rate and atomising air pressure in the bottom nozzle were kept constant at 16 mL/min and 50 psi, respectively.

The microgel particles were collected at the bottom of the chamber (see FIG. 3). The microgel particles in the solution were filtered and washed with deionised water three times to make sure that there was no remaining $CaCl_2$ in the formed microgel particles.

Results

1. Effect of some processing parameters on mean particle size of the gels was analysed using laser particle size analyser (Malvern). The results are presented in FIGS. 7-10. The results indicated that the mean size of the microgels ranged from 20 to 30 microns and it is possible to vary the size by regulating the atomising air pressure and alginate concentration. The effect of calcium chloride concentration on particle size was insignificant.
2. The particles were viewed under light microscope. The image of a sample is presented in FIGS. 11*a* and 11*b*. From the image and particle size analyser it was found the particles were not of the same size. However, it is possible to classify the particles and choose the range required for a particular application or choose an atomiser which gives a narrow particle size distribution.

This new technique quickly produces small size microgels. It is easy to operate. It consists of two identical upper and lower atomizers. Both atomizing nozzles are enclosed in a cylindrical chamber facing each other. Nozzles produce spray angle of 20° with spray height of 17.5 cm. Coating and gelling solutions atomized simultaneously resulting in large amount of small sized beads.

Advantages

Hydrocolloids and other non-toxic polymeric micro-particles have a range of uses in the pharmaceutical and food industries, for example, in the encapsulation of active food and the encapsulation and delivery of medicinal ingredients.

Examples 2-5

The potential pharmaceutical applications of the present invention for preparation of alginate gel microparticles include microencapsulation of conventional, small molecule entities and macromolecular biopharmaceuticals, vaccine formulation, microencapsulation of gene-based therapeutics and cells. A decided advantage of the technology lies in the use of water-based systems which avoids organic solvent-induced degradation of drug compounds and at the same time addresses health and safety issues and environmental concerns in keeping with moves towards 'green technologies'. The ease of scale-up from bench formulation to trials quantity is believed to be a particular strength of the processing technique. The following describes investigations aimed at microencapsulating four types of bioactive molecules in alginate gel microparticles to demonstrate the breadth of applications for the present invention. In particular, each entity for encapsulation was selected to illustrate the potential for encapsulating both conventional drugs and the new therapeutic macromolecules or biopharmaceuticals.

The four actives are:
1) conventional, low molecular weight (MW 206.3 Da) lipophilic drug—ibuprofen
2) conventional low MW (694-723 Da) hydrophilic antibiotic—gentamicin sulphate
3) macromolecular enzyme—lysozyme (MW 14.3 kDa)
4) polypeptide—insulin (MW 5.8 kDa)

Materials

Sodium alginate (Grindsted® alginate FD 155 DANISCO), calcium chloride (UNILAB), potassium phosphate buffer, ibuprofen, acetone, dichloromethane (DCM) was obtained from the BACS store, University of Queensland. Lysozyme (1 g, from chicken egg white, 50400 unit/mg, Sigma), BCA assay kit, QuantiPro™ assay kit, *Micrococcus lysodeikticus* suspension, insulin, gentamicin sulphate and ophthaldialdehyde (OPA) were purchased from Sigma-Aldrich, Australia.

Example 2

Micro Encapsulation of Lysozyme

Preparation of Lysozyme—Loaded Alginate Gel Microparticles

Sodium alginate was dissolved in distilled water at room temperature with stirring at a concentration of 2% (w/w). Lysozyme was first dissolved in distilled water (15 mL) to produce a 0.5% w/v solution, which was then added into 200 mL of alginate solution and dispersed thoroughly by homogenization using an IKA® Ultra-Turrax® T-10 Homogenizer at speed setting 2-3. The co-solution was sprayed into a mist of 200 mL 0.5M $CaCl_2$ solution using the methodology of the present invention at room temperature. Alginate solution and $CaCl_2$ solution were pumped through separate peristaltic pumps at a rate of 12 mL/min to upper and lower spray nozzles respectively, operating at an applied pressure of 50 Pa. Time of spraying depended on the time taken to pump through all the alginate solution but was typically around 45-60 minutes. The alginate beads which formed in the fine droplet mist of $CaCl_2$ solution were collected from the base of the spray chamber and washed three times by centrifugation in distilled water using a Rotofix 31A Centrifuge at 1000 rpm for 3 minutes.

Measurement of Lysozyme Loading of Alginate Gel Microparticles

The enzyme loading of alginate gel microparticles was determined following breakdown of freeze-dried microparticles in 0.5M sodium citrate pH 8.5 (2 mL). The particle suspension was incubated at room temperature (25° C.) for 24 hours until the particles disintegrated. The concentration of lysozyme was determined using the BCA assay (Sigma) by comparison with a calibration curve produced using a series dilution of lysozyme in sodium citrate (concentrations of 125, 200, 250 and 400 µg/mL). Lysozyme loading was expressed as the weight of enzyme per dry particle weight (% w/w).

Lysozyme Release from Alginate Microparticles in PBS

Samples of lysozyme-loaded alginate gel microparticles were re-suspended in distilled water and separated into triplicate 1 mL samples (average final concentration of alginate gel beads 14.85 mg/mL). The microparticle suspensions were incubated in 1 mL PBS (total of 2 mL suspension) at 37° C. over 10 days. The release medium was replaced completely by fresh PBS every 20 minutes in the first 2 hours then every 1 hour in the next 3 hours and subsequently at day 2, 5, 7. The gel microparticles were allowed to sediment during the release test, but were re-suspended before collection of release media and after adding fresh medium. The concentration of lysozyme in the release medium was determined by the BCA protein assay (Sigma). The amount of lysozyme released was calculated using a calibration curve produced using a series dilution of lysozyme in PBS (concentrations of 125, 200, 250 and 400 µg/mL) and expressed as cumulative release (%) versus time (days).

Lysozyme Release from Alginate Microparticles in HCl

A suspension (1 ml) of alginate microparticles containing lysozme was also retained in 1 ml HCl (0.05M) at 37° C. in a water bath over 2 hours. At 20 mins intervals, the HCl was removed completely and replaced by fresh HCl. The amount of lysozyme in the HCl release medium was analysed using the BCA assay and expressed as cumulative release (%) versus time. HCl was used as the blank solution during spectrophotometric assay of lysosyzme.

Activity Analysis of Released Lysozyme

The activity of lysozyme released from alginate gel microparticles in PBS was evaluated using a modified *Micrococcus lysodeikticus* assay (EC 3.2.1.17 Sigma). Lysozyme stock solution (200-400 U/ml) was prepared by dissolving 1000 U lysozyme from chicken egg white in 1 ml of 66 mM potassium phosphate buffer (pH 6.24) and a series dilution was prepared for construction of a calibration curve. *Micrococcus lysodeikticus* cell suspension (0.015% w/v) was used as the substrate working suspension. The lysozyme release medium was collected and stored at −20° C. prior to determination of the enzyme concentration by BCA assay and activity testing. Fresh lysozyme solution and lysozyme solution stored at 37° C. for 10 days were used as controls. After incubating a mixture of lysozyme solution (test and calibration samples) with *micrococcus lysodeikticus* cell suspension at 37° C. for 30 minutes, the absorption was measured at 450 nm. The activity of lysozyme released from the gel microparticles was determined by comparison with the activity of fresh lysozyme solution of the same concentration.

Investigation of the Morphology of Lysozyme-Loaded Alginate Microparticles Using Scanning Electron Microscopy (SEM)

The morphology of freeze dried alginate microparticles was examined using a Philips XL30 scanning electron microscope (SEM). Samples were mounted on aluminum sample stubs and sputter-coated with platinum using an Eiko-Sputter coater automatic mounting press prior to examination in the SEM at a voltage of 10 kV.

Measurement of Alginate Particle Size

The particle size of lysozyme-loaded alginate microparticles was determined by laser light scattering using a Mastersizer 2000 (Malvern Instruments). Particle size was expressed as the volume weighted mean diameter (D4, 3). The d(0.1), d(0.5) and d(0.9) values were also obtained to provide the maximum of the particle size range for 10, 50 and 90% of the particle population respectively.

Optical Microscopy

Alginate gel microparticles were examined using an optical microscope (Zeiss, AXIOSCOP 40) with camer a attachment (AXIOCam MRm).

Results

The particle size (D(4,3) value) of lysozyme-loaded alginate gel microparticles was measured at 44.4 µm by laser light scattering. The d(0.1), d(0.5) and d(0.9) values were respectively 16.0, 37.9 and 79.2 µm.

The lysozyme loading of dry gel microparticles was measured at 30-35% w/w.

Approximately 60% of the lysozyme content of the alginate gel microparticles was released in PBS at 37° C. in 1 day, 75% and 80% was released in 3 and 7 days respectively (FIG. 12).

When lysozyme-loaded alginate particles were incubated in HCl over 2 hours (0.05M, pH 1.2), no lysozyme was detected in the release medium.

Lysozyme released from the alginate gel microparticles in PBS at day 1, 3 and 10 retained 95-100% activity (FIG. 13).

Discussion

When preparing the lysozyme-alginate co-solution it was observed that the sodium alginate solution charged to a white coloration and this was accompanied by an increase in viscosity. Without wishing to be bound by theory, this behaviour could be explained by electrostatic interaction between the positively charged lysozyme molecules and the negatively charged alginate molecules, resulting in complex formation. The increased viscosity of the alginate-lysozyme co-solution could result in non-uniform processing and microparticle characteristics. Problems could arise, for example, with passage of the solution through the spraying nozzle under certain conditions but may be resolved if necessary by decreasing the concentration of alginate (2% to 1%) or lysozyme in the co-solution.

High loadings of lysozyme (30-35% w/w) were achieved in 30-40 μm alginate gel microparticles using the dual spray technique described here. This behaviour probably results from electrostatic interaction between the oppositely charged lysozyme and alginate molecules and physical chain entanglements in solution. Rapid release of lysozyme (60%) from the alginate gel microparticles was observed over the first 24 h in PBS at 37° C. and a further 20% of the enzyme load was gradually released over the following 6 days. In contrast no lysozyme was detected in 2 h in simulated gastric fluid using the BCA total protein assay. In addition, the enzyme which was released from alginate gel microparticles in PBS retained 95-100% activity. This finding indicates that bioactive macromolecules such as enzymes and the polypeptides could be protected from breakdown and loss of activity in the gastric fluid following oral administration and transported into the small and large intestine for absorption or to provide therapeutic effect.

Example 3

Microencapsulation of Gentamicin Sulphate

Preparation of Gentamicin Sulphate-Loaded Alginate Microparticles

All experiments carried out to encapsulate gentamicin sulphate (GS) in alginate gel microparticles by spraying of co-solutions was unsuccessful due to gelation of the alginate solution on contact with gentamicin sulphate solution. Therefore, unloaded alginate gel microparticles were incubated in GS solution to achieve drug diffusion into the microparticles.

Sodium alginate was dissolved in distilled water at a concentration of 2% (w/w). This solution was sprayed into a mist of 200 mL 0.5M $CaCL_2$ solution using the present invention at room temperature as described above. Alginate gel microparticles were collected and washed three times in distilled water. The residual distilled water was removed by centrifugation (3 minutes, 1000 rpm). The alginate gel microparticles were re-suspended in approximately 3 mL distilled water adding up to a total of 8 mL suspension, then immersed in GS solution (400 mg in 20 mL $H_2O$) at room temperature for 48 hours to achieve drug loading throughout the gel structure. Microparticles were collected and gently washed in distilled water followed by centrifugation at 1000 rpm for 3 minutes.

Measurement of GS Loading of Alginate Microparticles

The GS loading of alginate gel microparticles was determined following breakdown of freeze-dried samples in 0.5M sodium citrate pH 8.5 (2 mL). The suspension was incubated at room temperature (25° C.) for 24 hours until the particles disintegrated. The concentration of GS was determined by UV spectroscopy using an absorbance of 333 nm after derivatization with ophthaldialdehyde according to the method of Chang et al (1). The amount of gentamicin sulphate was calculated by comparison with a calibration curve produced using a series dilution of GS in sodium citrate (concentrations of 24, 48, 60, 96 and 120 μg/mL) and expressed as % w/w of the dried alginate particles.

Gentamicin Sulphate Release from Alginate Microparticles in PBS

GS-loaded alginate gel beads were re-suspended in 8 ml of distilled water. Suspensions (1 ml, average final concentration of alginate gel beads 41.8 mg/mL) were incubated in 1 mL PBS at 37° C. over 5 hours. The release medium was replaced completely by fresh PBS every 20 minutes in the first 2 hours then every 1 hour in the next 3 hours. The concentration of GS in the PBS release medium was determined by UV spectroscopy using an absorbance of 333 nm after derivatization with ophthaldialdehyde according to the method of Chang et al (1). The amount of gentamicin sulphate release was calculated by comparison with a calibration curve produced using a series dilution of GS in PBS (concentrations of 24, 48, 60, 96 and 120 μg/mL) and expressed as cumulative release (%) versus time (hr).

Characterisation of Particle Size and Morphology of GS-Loaded Alginate Microparticles The morphology and particle size of GS-loaded alginate microparticles were characterized according to the methods described above.

Results

The particle size of GS-loaded alginate microparticles (measured using optical microscopy) was in the range 10-20 μm when suspended in distilled water. However, the particle size expanded to around 30-50 μm after incubation in PBS release medium at 37° C. for 1 hour and further expansion occurred to 70-100 μm after 4 h. Particle breakdown to a clear gel occurred in 5 h. This behaviour may be explained by on ion exchange process in PBS which reduces $Ca^{2+}$ cross linking of the alginate matrix and subsequently decreases the gel strength.

The drug loading of gentamicin sulphate in alginate gel microparticles was measured at 30-35% w/w.

Approximately 90-95% w/w of the gentamicin sulphate load was released from the alginate gel particles in PBS at 37° C. in 5 hours (FIG. 14) and may be explained by expansion of the gel structure which facilitates diffusion of drug molecules into the external medium.

Discussion

Addition of gentamicin sulphate either in solution form or powder form into the alginate solution, resulted in immediate gel formation (believed to be due to interaction between the positively charged group on gentamicin sulphate and the negative alginate molecules). Therefore unloaded alginate gel beads were incubated in 2% gentamicin solution for 48 hours to achieve drug loading by molecular diffusion. Following incubation of the gel beads in gentamicin sulphate solution, the beads were found to shrink to around 10-20 μm compared with the original bead diameter which was in the range of 30-40 μm. However, the gel beads expanded significantly to 70-100 μm after incubating in PBS at 37° C. over 4 hours. This behaviour could be explained by the strong positively charged gentamicin sulphate molecule de-stabilising the alginate-calcium complex which accelerated the rate of exchange of $Ca^{2+}$ with $Na^+$ from the PBS medium. The resultant rapid release behavior may be useful for local delivery of antibacterials into a wound bed from topically applied alginate gel beads.

Example 4

Micro Encapsulation of Insulin

Preparation of Insulin-Loaded Alginate Gel Microparticles

Sodium alginate was dissolved in distilled water at a concentration of 2% (w/w). Insulin (50 mg) from bovine pancreas (Sigma) was first dissolved in 0.1M HCl (10 mL) then adjusted to pH 7 with 0.1M NaOH. The insulin solution was added into 100 mL of alginate solution and dispersed thoroughly by homogenizing. This solution was sprayed into a droplet mist of 80 mL, 0.5M $CaCl_2$ solution using the Present invention at room temperature. Alginate and $CaCl_2$ solutions were pumped through peristaltic pumps at a rate of 12 mL/min to upper and lower spray nozzles respectively and the pressure applied to each spray nozzle was set at 50 Pa. The alginate gel beads which collected in the base of the spray chamber were collected and washed three times in distilled water by centrifugation at 1000 rpm for 3 minutes.

Measurement of Insulin Loading of Alginate Gel Microparticles

The insulin loading of alginate gel beads was determined following breakdown of freeze-dried particles in 0.5M sodium citrate pH 8.5 (2 mL). The particle suspension was incubated at room temperature (25° C.) for 24 hours until the particles disintegrated. The concentration of insulin was determined using the BCA assay described above. Insulin loading was expressed as the weight of insulin per dry particle weight (% w/w).

Insulin Release from Alginate Gel Microparticles in PBS

Insulin-loaded alginate gel microparticles were re-suspended in 2 mL distilled water and separated into triplicate 1 mL suspensions (average final concentration of alginate gel beads 38.9 mg/mL). Microparticle suspensions (1 mL) were incubated in 2 mL PBS (total 3 mL suspension) at 37° C. over 10 days. The release medium was replaced completely by fresh PBS every 20 minutes in the first 2 hours then every 1 hour in the next 3 hours, and subsequently at day 2, 5, 7, 10. The concentration of insulin in the samples was determined by the QuantiPro™ BCA Assay Kit (Sigma). The amount of insulin release was calculated using a calibration curve produced using a series dilution of insulin in PBS (concentrations at 5, 10, 15, 20 and 25 µg/mL) and expressed as cumulative release (%) versus time (days).

Insulin Release from Alginate Gel Microparticles in HCl

A suspension of alginate microparticles (1 ml) containing insulin was retained in 1 ml HCl (0.05M) at 37° C. in a water bath over 2 hours. At 20 min intervals, the HCl was removed completely and replaced by fresh HCl. The amount of insulin in the HCl release medium was analysed using the BCA assay and expressed as cumulative release (%) versus time. HCl was used as the blank solution.

Characterisation of Particle Size and Morphology of Insulin-Loaded Alginate Gel Microparticles The morphology of insulin-loaded alginate gel microparticles and the particle size were characterized according to the methods described above.

Results

The particle size of insulin-loaded alginate gel microparticles was measured in the range 30-40 µm using optical microscopy.

The insulin loading of the alginate gel beads was measured in the range of 25-30% w/w.

Approximately 11% of the insulin load was released from alginate gel beads in PBS at 37° C. in 1 day; 19 and 38% were released in 3 and 10 days, respectively (FIG. 15).

Importantly, no insulin was detected in the release medium when insulin-loaded alginate beads were incubated in HCl for 2 hours (0.05M/ml pH 1.2).

Discussion

Insulin may be readily incorporated in alginate gel particles less than 50 µm in size at high loadings (25-30% w/w) using the Present invention. The alginate gel beads-containing insulin were completely broken down in PBS at day 10 forming a gel-like substance. Without being limited to theory, this behaviour can be explained by $Na^+$ ions in PBS gradually replacing the $Ca^{2+}$ crosslinking ions in the alginate—$Ca^{2+}$ complex overtime, resulting in degradation of the gel structure. Less than the 50% of the insulin content of the microparticles had been released by day 10 indicating interaction between the insulin molecules and alginate.

No insulin was detected by BCA assay in the release medium when insulin-loaded alginate gel particles were incubated for 2 h in simulated gastric fluid (HCl, pH 1.2). This finding seems to suggest that polypeptides such as insulin could be protected from breakdown and loss of activity in the gastric fluid following oral administration and transported into the small and large intestine for absorption or to provide therapeutic effect.

Example 5

Microencapsulation of Ibuprofen

Preparation of Ibuprofen-Loaded Alginate Microparticles Using Dispersions of Ibuprofen Particles in Alginate Solution Sodium alginate was dissolved in distilled water at a concentration of 1% (w/v). Ibuprofen (1 g) was first dissolved in acetone (15 mL) and the solution was added into 200 mL of alginate solution and dispersed thoroughly by homogenizing. This solution was sprayed into a droplet mist of 100 mL 0.5M $CaCL_2$ solution using the present invention at room temperature. Both alginate and $CaCl_2$ solution were pumped through peristaltic pumps at a rate of 12 mL/min to upper and lower spray nozzles respectively. The pressure applied to each spray nozzle was set at 50 Pa. Alginate gel beads were collected from the base of the spray chamber and washed three times in distilled water followed by centrifugation at 1000 rpm for 3 minutes.

Reduction of Ibuprofen Particle Size for Microencapsulation

The particle size of the 'as received' ibuprofen powder was found to range from 30-100 micron which is above the range of 10-50 µm observed for the alginate gel microparticles produced by the Present invention. Therefore, it was necessary to reduce the particle size of ibuprofen powder for efficient encapsulation in alginate gel beads. The first approach was to dissolve the ibuprofen powder in acetone and then disperse the ibuprofen solution in the alginate solution prior to microencapsulation.

According to the British Pharmacopoeia 2008, ibuprofen is practically insoluble in water, but freely soluble in acetone, methanol and dichloromethane (DCM). Ibuprofen also dissolves in dilute solutions of alkali hydroxides and carbonates. Solvents including distilled water, ethanol, methanol, isopropanol and acetone were used to dissolve ibuprofen and acetone was selected for formulation studies. Ibuprofen was first dissolved in a minimum volume of acetone (to avoid increasing the viscosity of alginate solution on mixing). The ibuprofen/acetone solution was added to the alginate solution drop-wise and dispersed using an IKA® Ultra-Turrax® T-10 Homogenizer at a speed setting of 2-3. Re-crystallisation of ibuprofen occurred on adding the ibuprofen/acetone solution to the alginate solution. The particle size of the crystals was measured using an optical microscope and found to be around 10-15 microns. The crystals were generally cubic or rectangular in form with a thin longitudinal shape. The approach described enabled the ibuprofen particle size to be successfully reduced to an encapsulatable range.

When alginate solution (2% w/w) with dispersed ibuprofen powder of reduced particle size was pumped through a peristaltic pump at a rate of 12 mL/min to the upper spray nozzle, the nozzle blocked after a short while due to gelatinization of the high viscosity alginate/acetone/water solution. Encapsulation was therefore discontinued. This problem was resolved by reducing the concentration of alginate solution to 1% w/w and evaporating off the acetone from the alginate/ibuprofen dispersion by stirring overnight Stabilisation of Ibuprofen Dispersions in Alginate Solution Using Surfactants If encapsulation is not carried out immediately after dispersion of ibuprofen in alginate solution, sedimentation of the ibuprofen crystals can occur resulting in crystal aggregation and influencing the efficiency of drug encapsulation. Taking this potential problem into consideration, ibuprofen dispersions in alginate solution were prepared with addition of a commonly used surfactant, e.g. PVP40 (4% w/v). A solution of PVP40 in water (10 mL, 4% w/v) was prepared and added while stirring into an ibuprofen solution in acetone (10 mL, 5% w/v) achieving a 50:50 ratio of PVP:acetone. The acetone (80%) was then partially evaporated off using a rotary evaporator. Before ibuprofen recrystallisation occurred, the PVP/acetone-ibuprofen solution was added to the alginate solution and dispersed using a IKA® Ultra-Turrax® T-10 Homogenizer. The aim of this approach is to use the PVP surfactant to keep the ibuprofen crystals well dispersed during encapsulation, and to avoid gelation and subsequent blockage of the spray nozzle by having a minimum amount of acetone present in the alginate solution.

Ibuprofen Release from Alginate Gel Microparticles in PBS

Samples of ibuprofen loaded-alginate microparticles were re-suspended in 2 mL distilled water and separated into triplicate 1 mL suspension. The suspensions were incubated in 2 mL PBS at 37° C. over 10 days. The release medium was replaced completely by fresh PBS every 20 minutes in the first 2 hours then every 1 hour in the next 3 hours, and subsequently at day 2, 5, 7, 10. The concentration of ibuprofen in the PBS release medium was analysed using a HITACHI U-1800 spectrophotometer by measuring the UV absorbance at 264 nm. The amount of ibuprofen release was calculated using a calibration curve and expressed as cumulative release (%) versus time (days).

The solubility of ibuprofen in PBS is limited (300 µg/ml), therefore the stock solution of ibuprofen was prepared by adding 300 mg of ibuprofen in PBS (1 L) by with vigorous stirring until no particles were visible. The calibration curve was produced using a series dilution of ibuprofen in PBS (concentrations at 100, 150, 200, 250 and 300 µg/mL).

Results

The ibuprofen powder size was reduced by precipitation from acetone from a size of 30-40 microns to around 10-15 microns. The particle size (optical microscopy) of ibuprofen-loaded alginate gel microparticles produced by spraying a dispersion of ibuprofen in alginate solution into a $CaCl_2$ mist was 45-50 µm.

The ibuprofen loading of alginate gel particles estimated from measurements of optical micrographs (FIG. 16) was found to be 10-15% v/v.

Separation of Unencapsulated Ibuprofen from Alginate Gel Microparticles

Experiments were carried out to differentiate between unencapsulated and microencapsulated drug since release experiments revealed that excessive amounts of ibuprofen were associated with the alginate gel microparticles and the optical micrographs may be showing unencapsulated ibuprofen. The first approach involved washing the particles with acetone to dissolve un-encapsulated ibuprofen. However, since the particles are porous, acetone may enter the beads and dissolve the encapsulated ibuprofen.

The second approach was to freeze-dry the gel microparticles after encapsulation followed by washing once in acetone and then centrifuging to remove the residual acetone. The dried particles were re-suspended in PBS prior to the release study. However, after re-hydrating the freeze-dried beads (following treatment with acetone) it was observed (using optical microscopy) that the beads did not retain the original spherical shape of the hydrated state. It was considered that addition of acetone to the freeze-dried beads may have caused this effect. However, freeze-dried lysozyme-encapsulated alginate gel beads were also found to be fragmented on rehydration. Freezing at −80° C. before freeze-drying probably ruptures the alginate-calcium complex due to water expansion, resulting in fragmentation after freeze-drying (FIG. 17). The step of adding acetone to the freeze-dried beads to remove unencapsulated ibuprofen would thus have removed the encapsulated ibuprofen. This was evidenced under the optical microscope since almost no ibuprofen crystals were observed after washing freeze-dried alginate beads with acetone.

The third approach to evaluate ibuprofen loading of alginate gel particles involved removing unencapsulated ibuprofen from the hydrated beads. Dichloromethane (DCM) was used as the solvent since it is immiscible with water and formed a separate layer beneath the water phase which was removed using a separating funnel. The alginate beads were retained in the hydrated state with spherical shape (confirmed under the optical microscope). Immiscibility of DCM and water is anticipated to prevent the solvent entering the gel particles resulting in limited removal of entrapped ibuprofen.

SEM examination of alginate gel microparticles or protein/drug-loaded alginate microparticles revealed that freeze drying damages the alginate particles resulting in fragmentation (FIG. 17A-C). The remnant of a 20 µm lysozyme-loaded alginate particle may be visible in FIG. 17D (arrowed). ESEM or cryo-SEM is required to show the morphology of alginate microparticles in hydrated form.

Production of Ibuprofen Loaded Alginate Gel Microparticles by Drug Diffusion into Unloaded Microparticles This approach was based on the diffusion method for loading alginate gel microparticles with gentamicin sulphate. Blank alginate gel microparticles were prepared as described above. Ibuprofen (500 mg) was dissolved in 20 ml acetone and the solution was added to a suspension of the unloaded (blank) alginate microparticles in distilled water. This approach was unsuccessful due to spontaneous crystallisation of ibuprofen on contact of the ibuprofen/acetone solution with the aqueous particle suspension. Aggregation of the alginate gel particles also occurred, possibly due to dehydration on contact with acetone.

Preparation of Ibuprofen-Loaded Alginate Microparticles by Drug Diffusion from Ibuprofen Solution in Sodium Hydroxide Sodium alginate was dissolved in distilled water at a concentration of 2% (w/w) and sprayed into 200 mL 0.5M $CaCL_2$ solution using the Present invention at room temperature as described above. Alginate gel beads were collected and washed three times in distilled water. The residual distilled water was removed by centrifugation (3 minutes, 1000 rpm). The alginate gel beads were re-suspended in approximately 5 mL distilled water adding up to a total of 10 mL suspension, then immersed in 30 ml of 1% ibuprofen solution in 0.1M NaOH at room temperature overnight to achieve drug loading throughout the gel structure. Beads were collected and then gently washed in distilled water followed by centrifugation at 1000 rpm for 3 minutes. Samples used for drug loading experiments had been stored at 5° C. for at least month.

Measurement of Ibuprofen Loading in Alginate Microparticles

The ibuprofen loading of alginate gel microparticles was determined following breakdown of freeze-dried samples in 0.5M sodium citrate pH 8.5 (2 mL). The particle suspension was incubated at room temperature (25° C.) for 24 hours until the particles disintegrated. The concentration of ibuprofen was determined by UV spectroscopy using an absorbance of 265 nm. The amount of ibuprofen in the gel microparticles was calculated by comparison with a calibration curve produced using a series dilution of ibuprofen in sodium citrate (concentrations at 50, 100, 150, 200 and 300 µg/mL). The ibuprofen loading was expressed as the weight per dry particle weight (% w/w).

Ibuprofen Release from Alginate Microparticles in PBS

Ibuprofen-loaded alginate gel beads were re-suspended in 15 ml of distilled water and separated into triplicate 2 mL suspensions. The suspensions were incubated in 2 mL PBS at 37° C. over 3 days. The release medium was replaced completely by fresh PBS every 1 hour in the first 6 hours then every 1 day in the next 3 days. The concentration of ibuprofen in the PBS release medium was determined by UV spectroscopy using an absorbance of 265 nm. The amount of ibuprofen release was calculated by comparison with a calibration curve produced using a series dilution of ibuprofen in PBS (concentrations at 50, 100, 150, 200 and 300 µg/mL) and expressed as cumulative release (%) versus time (hr).

Characterisation of Particle Size and Morphology of Ibuprofen-Loaded Alginate Gel Microparticles The morphology and particle size was characterized according to the methods described above.

Results

The particle size (optical microscopy) of ibuprofen-diffusion loaded alginate microparticles was in the range 30-40 µm when suspended in ibuprofen-NaOH solution and the particle size was maintained at around 30-40 µm in PBS release medium at 37° C. for the first day. The particles had broken down by day 3.

The ibuprofen loading of alginate gel microparticles produced by diffusion loading was measured at 25-30% w/w.

Approximately 90% w/w of the ibuprofen content of alginate gel particles was released in PBS in 6 hours (FIG. 18) followed by a gradual release of the remainder over 3 days.

Discussion

Figure 5:
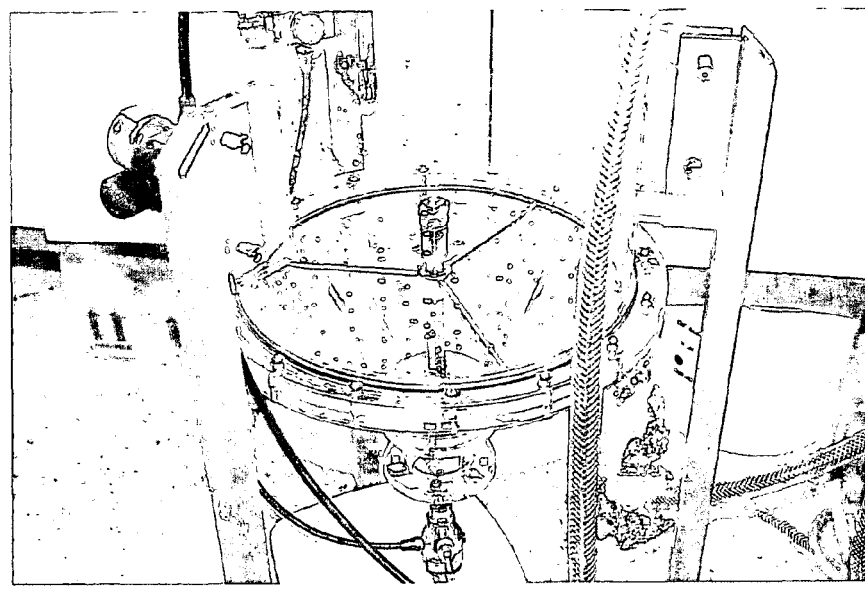
FIG. 5 shows a photographic representation of the bottom of the reactor of FIG. 1.

Ibuprofen-loaded alginate gel particles 45-50 µm in size have been produced by spraying a dispersion of ibuprofen particulates in alginate solution into a $CaCl_2$ mist using the Present invention. The ibuprofen loading of the alginate gel particles estimated from measurements of optical micrographs (FIG. 5) was found to be 10-15% v/v. This approach requires careful control of the size of the dispersed drug particles to ensure efficient encapsulation. Uncertainties exist at present concerning the ratio of unencapsulated to encapsulated ibuprofen which prevents reliable measurement of drug loading and release behaviour.

Alginate gel particles of around 30-40 µm incorporating high loadings of ibuprofen (25-30%) were produced by diffusion loading of blank gel particles produced by the Present invention. Rapid release of most of the drug load (90%) occurred in PBS in 6 hours. This release behaviour would be advantageous for delivering steroids to the small intestine after passage through the stomach.

Conclusions

The dual spray technology of the present invention for alginate gel microparticles production has been applied successfully to encapsulate conventional drugs (ibuprofen steroid, gentamicin sulphate antibiotic) and macromolecular bioactive entities (lysozyme enzyme and insulin). A firm foundation and knowledge base has been established which invites further investigation of the process for manufacturing new and existing pharmaceuticals.

Example 6

Fish Oil Encapsulation

The oil-loaded alginate microcapsules were found to contain numerous minute globules of fish oil, which were entrapped in spherical microcapsules as the sodium alginate droplets react with $Ca^{2+}$ ions. No fishy smell was detected in freshly made oil-loaded microcapsules. In initial food application trials, oil-loaded microcapsules were mixed in with food products to observe changes to sensory properties. Small quantities (3 g) of microcapsules were added to milk, orange juice and mayonnaise (300 mL). In all food products, no fishy smell was detected. Food appearances were not affected by addition of microcapsules. Furthermore, addition of microcapsules did not affect taste of food products. This indicates that odours and taste have been masked by microencapsulation.

The spray aerosol system was able to produce alginate microcapsules quickly and easily. Oil-loaded microcapsules recovered were ⅓ (volume) of the sodium alginate originally used. Microencapsulation was continuous. When 300 mL sodium alginate solution (2.5% w/w) was sprayed in the encapsulation chamber at 60 psi and 12 ml/min, the process lasted for 30 minutes. In theory, the only limiting factor to the speed of microcapsules production is the rate of delivery of sodium alginate solution into the nozzle. Hence, by employing a continuous flow and extending the time of spraying, a larger scale of production can be achieved.

It was observed that freshly produced oil-loaded microcapsules were prone to agglomeration. Storage and gentle stirring did not reduce agglomeration. Agglomeration or aggregation of particles is a common occurrence in alginate microcapsules produced by air atomising. (Cui et al. 2001) reported aggregation of alginate microcapsules due to lack of proper atomisation when the distance between atomising nozzle and calcium bath was too short. Other workers also reported agglomeration in drug-loaded alginate microcapsules. Agglomeration of the alginate microcapsules were indicated by large particle size (100-300 µm) in less than 90% d(0.9) of the sample.

After the completion of encapsulation, the newly formed alginate microcapsules were washed with distilled water to remove excess Ca²⁺ ions. Microcapsules were centrifuged (3000 rpm, 3 mins) gently and subsequently washed with distilled water and stored.

Effect of Fish Oil Concentration on Particle Size

The increase of fish oil concentration in alginate microcapsules corresponds to a significant decrease in particle size (see FIG. 19). This result is dissimilar to results obtained by other workers (Cui et al. 2001). The increase of oil content in an emulsion where the amount of surfactant is constant causes an increase in EDS due to the limited amount of surfactant present to emulsify the oil. Hence, it is expected that microcapsule size will also increase corresponding to the size increase of oil droplets (Chan, Lim & Heng 2000).

The highly significant change in particle size suggests two possible causes. The presence of fish oil emulsion interferes with the matrix structure of alginate microcapsules and causes shrinkage by syneresis. Interference may be caused when oil droplets displaces water molecules. However, no report of the effects of core material on the particle size of alginate microcapsules could be found in literature. A second possibility is that as fish oil concentration is increased, the viscosity of sodium alginate solution is reduced due to the viscosity effect of fish oil emulsion. The decrease in sodium alginate viscosity corresponds to a smaller microcapsule particle size.

Dispersability Test

Oil-loaded alginate microcapsules were stored in varying concentrations of sucrose solution to observe the effect of solute concentrations on the size of microcapsules. Studies on the effect of ionic strength and pH on alginate microcapsule have been reported extensively. However, not much have been studied about the effects of solute concentrations.

Our results showed that particle size of alginate microcapsules undergo significant swelling when sucrose concentration was above 1% (w/w) (FIG. 20). However further increase of sucrose concentrations did not cause anymore swelling to the microcapsules (p=0.34). The observations were not as expected. An increase in osmotic pressure when sucrose concentration was increased was expected to cause shrinkage of alginate microcapsules. Osmotic pressure difference causes alginate microcapsules to lose water molecules to the surroundings.

Double Encapsulation Product

Oil-loaded alginate microcapsules were spray dried in maltodextrin (DE=10). The resulting powder consists of fish oil droplets encapsulated by 2 layers of hydrocolloid—alginate and maltodextrin, and a layer of surfactant—Hi-Cap. Spray dried powder was free flowing and similar coloured to maltodextrin (FIG. 21). Studies on the spray drying of calcium alginate gels are currently not available. Double encapsulation is generally achieved by spray coating microcapsules in waxes, vegetable oil or fats (Cho & Park 2002; Onwulata, Konstance & Holsinger 1998). A second encapsulating coat provides a better barrier to moisture uptake, pH change, temperature change and reactive chemicals, and thus maintaining powder stability during storage (Cho & Park 2002). The use of maltodextrin in this study functions as an added barrier to oxidation as carbohydrates show excellent oxygen blocking properties (Thies 2001).

Double encapsulation by spray drying is also a novel method of drying oil-loaded alginate microcapsules formed by spray aerosol method. Measured moisture content of spray dried oil-loaded microcapsules were measured and compared (Table 1). The moisture content of spray dried microcapsules ranged from 1.70±0.10 to 5.00±0.90% w/w. Methods used to dry alginate microcapsules by current workers include drying in oven, isopropyl alcohol and fluidised air column (Chan, Lim & Heng 2000). A number of limitations exist for these methods. Drying in oven causes caking which results in hard and brittle alginate microcaspules. As a solvent for oil, the use of isopropyl alcohol will cause leaching of oil from alginate microcapsules. This method of drying may be more advantageous that other drying method due to short drying time. The problem of surface oil generally associated with encapsulation of volatile oil by spray drying can also be also minimised due to the fact that most of the oil droplets are already encapsulated inside alginate microcapsules.

TABLE 1

Moisture content of spray dried fish oil microcapsules.

| Mass of alginate (g) | Mass of fish oil (g) | Mass of Hi-Cap (g) | Solid content (microcapsule) (%) | Hi-Cap: Fish oil | Moisture content (w/w %) (Mean ± SD) |
|---|---|---|---|---|---|
| 4.5 | 4 | 4 | 4.2% | 1:1 | 5.00 ± 0.90 |
| 4.5 | 12 | 4 | 6.8% | 1:3 | 1.70 ± 0.10 |
| 4.5 | 20 | 4 | 9.5% | 1:5 | 3.30 ± 0.09 |
| 4.5 | 25 | 5 | 11.5% | 1:5 | 2.90 ± 0.15 |
| 6 | 4 | 4 | 4.7% | 1:1 | 3.40 ± 0.12 |
| 6 | 12 | 4 | 7.3% | 1:3 | 2.30 ± 0.10 |
| 6 | 25 | 5 | 12.0% | 1:5 | 2.90 ± 0.20 |
| 6 | 20 | 4 | 10.0% | 1:5 | 2.60 ± 0.16 |
| 6 | 32 | 4 | 14.0% | 1.8 | 2.80 ± 0.14 |

Rehydration of Spray Dried Powder

The reconstitution of spray dried oil-loaded alginate microcapsules by hydration in water were studied. A major property of dehydrated emulsions and encapsulated bioactives is the ease of reconstitution (Vega & Roos 2006). It is essential that the rehydrated particles revert to the condition that resembles the undried material. For encapsulated bioactives such as fish oil, it is crucial that the reconstitution of spray dried powder do not alter the properties of the core material and that the core content is unchanged from pre-dried state.

Complete rehydration of spray-dried microcapsules was achieved after about 30 minutes. This was indicated by no significant changes (p=0.86) to size distribution of microcapsules after 30 minutes of rehydration in water (FIG. 22). The reconstitution process in water can be divided into 4 steps: wetting, dispersion, and dissolving (Vega & Roos 2006). Wetting of the particles is often the reconstitution rate-controlling step. Wetting describes the capacity of the powder particles to absorb water on their surface under the influence of capillary forces. However, smaller particles may clump together to share a wetted surface layer in the initial stages of reconstitution (Ortega-Rivas 2005). This is due to the large surface:mass ratio of small particles which may impede wetting. This may explain the decrease of particle size after initial reconstitution (0 minutes after rehydration and 30 minutes after rehydration).

In our powder samples, the relatively long period taken for complete rehydration of powder may be attributed to a few factors. The nature of the powder surface such as presence of free fat, can limit wettability (Ortega-Rivas 2005). Fish oil may have been deposited on the surface of the alginate microcapsule powders during spray drying. The presence of surface-active agents also plays a role in wetting (Vega & Roos 2006). Hygroscopic components will yield good wetting property. The low dextrose equivalent (DE=10) of the maltodextrin used as second encapsulation layer is less hygroscopic (Thies 2001).

Our results showed that reconstituted oil-loaded alginate microcapsules do not possess the same size distribution as the original pre-dried state (FIG. 23). This phenomenon was observed in all reconstitution tests for powders of different composition of sodium alginate, Hi-Cap and fish oil. Volume weighted mean, D[4,3], of particles decreases in the rehydrated state (FIG. 23). Volume weighted mean is influenced by large particles (O'Hagan et al. 2005). d(0.9), which is also a measure of larger particles also decreases. These two factors suggest a decrease in size for larger microcapsule particles. The decrease in particle size may be due to the breakdown of agglomeration of alginate microcapsules. The presence of maltodextrin in the mixture may play a role in breaking the alginate microcapsules agglomeration. It has been shown that maltodextrin, in the presence of hydrocolloids, aids in dispersion and proper hydration with minimal clumping. Agglomeration is avoided due to structural heterogeneity of the compounds, which discourages crystallisation but encourages solubility. Image analysis of the pre-dried and rehydrated microcapsules (FIG. 24) showed that there is an obvious break down of larger microcapsule particles in the rehydrated microcapsules.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method for preparing microparticles comprising impacting and intimately mixing an aerosol of a first cross-linkable reagent with an aerosol of a second cross-linking reagent to thereby form microparticles, wherein the aerosols are formed using respective atomizers that are arranged facing each other.

2. The method according to claim 1, wherein formation of the microparticles takes place by a sol-gel phase transition associated with the cross-linkable reagent.

3. The method according to claim 1, wherein the cross-linkable reagent is an alginate and the cross-linking reagent comprises a divalent or trivalent cation.

4. The method according to claim 1, wherein an active is incorporated into microparticles as the microparticles are produced.

5. The method according to claim 4, wherein the active is provided in solution with the cross-linkable or cross-linking reagent, or as a suspension of particles of the active in a solution of the cross-linkable or cross-linking reagent, so that the aerosol produced comprises droplets including a combination of active and reagent.

6. The method according to claim 1, wherein an active is incorporated into the microparticles after the microparticles have been formed by exposure of microparticles to a solution of the active.

7. The method of claim 4, wherein the active is selected from the group consisting of probiotics, micro-organisms, viruses, oils, pharmaceuticals, enzymes, vitamins, cosmeceuticals, dies, inks and agricultural actives.

8. The method according to claim 1, further comprising coating microparticles produced in accordance with the method with cross-linkable reagent and contacting the coated microparticles with further cross-linking agent so as to develop a multi-layer or thicker coating on the microparticles.

9. The method according to claim 1, wherein the mixing is performed in a reaction chamber.

10. The method according to claim 1, wherein the method further comprises extracting the microparticles from the reaction chamber.

11. The method according to claim 10, wherein the method further comprises separating the extracted microparticles from any reagents.

12. The method according to claim 11, wherein the method further comprises separating the extracted microparticles using at least one of:
   a centrifugal separator;
   a clarifier; and
   a filter.

13. A reactor for implementing the method claimed in claim 1, the reactor comprising a reaction chamber comprising a first atomizer for introducing an aerosol of a cross-linkable reagent into the reaction chamber, and a second atomizer for introducing an aerosol of a cross-linking reagent into the reaction chamber, wherein the first and second atomizers face each other to achieve impact and intimate mixing of the aerosols.

14. A method, comprising:
   (a) impacting and intimately mixing an aerosol of a first cross-linkable reagent with an aerosol of a second cross-linking reagent to thereby form microparticles, wherein the aerosols are formed using respective atomizers that are arranged facing each other, and
   (b) encapsulating an active ingredient with the microparticles.

15. The method according to claim 2, wherein the cross-linkable reagent is an alginate and the cross-linking reagent comprises a divalent or trivalent cation.

16. The method of claim 6, wherein the active is selected from the group consisting of probiotics, micro-organisms, viruses, oils, pharmaceuticals, enzymes, vitamins, cosmeceuticals, dies, inks and agricultural actives.

* * * * *